(12) United States Patent
Nomura et al.

(10) Patent No.: US 8,273,898 B2
(45) Date of Patent: Sep. 25, 2012

(54) OXADIAZOLE DERIVATIVE, LIGHT-EMITTING ELEMENT, DISPLAY DEVICE, LIGHTING DEVICE, AND ELECTRONIC DEVICE

(75) Inventors: Hiroko Nomura, Fukuoka (JP); Sachiko Kawakami, Atsugi (JP); Nobuharu Ohsawa, Zama (JP); Satoshi Seo, Kawasaki (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 177 days.

(21) Appl. No.: 12/730,287

(22) Filed: Mar. 24, 2010

(65) Prior Publication Data

US 2010/0244669 A1 Sep. 30, 2010

(30) Foreign Application Priority Data

Mar. 27, 2009 (JP) .................. 2009-079914

(51) Int. Cl.
*C07D 271/10* (2006.01)
*B32B 9/00* (2006.01)
*H01J 1/62* (2006.01)
(52) U.S. Cl. ........ 548/143; 548/125; 313/504; 313/506; 428/690; 428/917
(58) Field of Classification Search .......... 548/125, 548/143; 313/504, 506; 315/169.3; 428/690, 428/917
See application file for complete search history.

(56) References Cited

U.S. PATENT DOCUMENTS

| | | | |
|---|---|---|---|
| 5,420,288 A | 5/1995 | Ohta et al. | |
| 5,610,309 A | 3/1997 | Ohta et al. | |
| 6,329,084 B1 | 12/2001 | Tamano et al. | |
| 6,593,013 B2 | 7/2003 | Nii et al. | |
| 6,784,318 B2 | 8/2004 | Shirota et al. | |
| 6,797,848 B2 | 9/2004 | Hosokawa et al. | |
| 7,038,086 B2 | 5/2006 | Shirota et al. | |
| 7,723,722 B2 * | 5/2010 | Kawakami et al. | 257/40 |
| 7,898,171 B2 * | 3/2011 | Egawa et al. | 313/504 |
| 2007/0222376 A1 | 9/2007 | Ohsawa et al. | |
| 2008/0230747 A1 | 9/2008 | Nomura et al. | |

FOREIGN PATENT DOCUMENTS

CN 1854136 11/2006
CN 1919842 2/2007

OTHER PUBLICATIONS

Baldo et al., "Very High-Efficiency Green Organic Light-Emitting Devices Based on Electrophosphorescence," Applied Physics Letters, Jul. 5, 1999, vol. 75, No. 1, pp. 4-6.
Adachi et al., "Electroluminescence in Organic Films with Three-Layer Structure," Japanese Journal of Applied Physics, Feb. 20, 1988, vol. 27, No. 2, pp. L269-L271.
Leung et al., "The Unusual Electrochemical and Photophysical Behavior of 2,2'-Bis(1,3,4-oxadiazol-2-yl)biphenyls, Effective Electron Transport Hosts for Phosphorescent Organic Light Emitting Diodes," Organic Letters, 2007, vol. 9 , No. 2 , pp. 235-238.
Guan et al., High Performance Blue Electroluminescent Devices Based on 2-(4-biphenylyl)-5-(4-carbazole-9-yl)phenyl-1,3,4-oxadiazole, Chemical Communications, 2003, pp. 2708-2709.
Search Report (Application No. 08005224.4) dated Jul. 17, 2008.
Tang. C et al., "Organic Electroluminescent Diodes," Applied Physics Letters, Sep. 21, 1987, vol. 51, No. 12, pp. 913-915.

* cited by examiner

*Primary Examiner* — Golam M M Shameem
(74) *Attorney, Agent, or Firm* — Eric J. Robinson; Robinson Intellectual Property Law Office, P.C.

(57) ABSTRACT

Provided is a bipolar substance having high excitation energy, in particular, high triplet-excitation energy. An oxadiazole derivative represented by General Formula (G1) below is provided (G1)

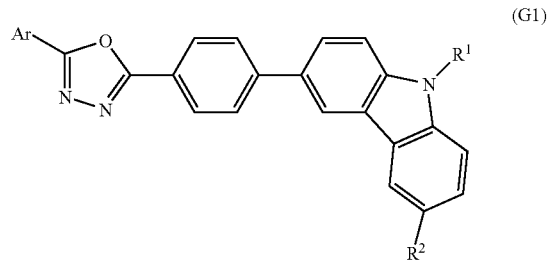

In the formula, Ar represents a substituted or unsubstituted aryl group having 6 to 10 carbon atoms in a ring. $R^1$ represents an alkyl group having 1 to 4 carbon atoms or a substituted or unsubstituted aryl group having 6 to 10 carbon atoms in a ring. $R^2$ represents hydrogen, an alkyl group having 1 to 4 carbon atoms, or a substituted or unsubstituted aryl group having 6 to 10 carbon atoms in a ring.

20 Claims, 19 Drawing Sheets

Highest Occupied Molecular Orbital (HOMO)

Lowest Unoccupied Molecular Orbital (LUMO)

Highest Occupied Molecular Orbital (HOMO)

Lowest Unoccupied Molecular Orbital (LUMO)

OXADIAZOLE DERIVATIVE, LIGHT-EMITTING ELEMENT, DISPLAY DEVICE, LIGHTING DEVICE, AND ELECTRONIC DEVICE

BACKGROUND OF THE INVENTION

1. Field of the Invention

The present invention relates to oxadiazole derivatives; light-emitting elements including the oxadiazole derivatives; and display devices, lighting devices and electronic devices each using the light-emitting element.

2. Description of the Related Art

In recent years, research and development of light-emitting elements using electroluminescence have been extensively conducted. In a basic structure of such a light-emitting element, a layer including a light-emitting substance is interposed between a pair of electrodes. By applying voltage to this element, light emission can be obtained from the light-emitting substance.

Since this type of light-emitting element is a self-luminous type, it has advantages over a liquid crystal display in that visibility of an image is high and that no backlight is needed, and is thought to be suitable as flat panel display elements. Further, such a light-emitting element also has advantages in that the element can be formed thin and lightweight and that response time is extremely high.

Further, since this type of a light-emitting element can be formed to have a film shape, surface light emission can be easily obtained by formation of large-area elements. This feature is difficult to realize with point light sources typified by a filament lamp and an LED or with linear light sources typified by a fluorescent light. Such light-emitting elements therefore have a high utility value as a surface light source that can be applied to lighting devices or the like.

Light-emitting elements using electroluminescence are broadly classified depending on whether they use an organic compound or an inorganic compound as a light-emitting substance. When an organic compound is used as a light-emitting substance, by application of voltage to a light-emitting element, electrons and holes are injected from a pair of electrodes into a layer including the light-emitting organic compound, and current flows. Carriers (i.e., electrons and holes) then recombine to excite the light-emitting organic compound. The light-emitting organic compound relaxes to a ground state from the excited state, emitting light.

The light-emitting element which works on this principle is called a current-excitation light-emitting element. Note that an excited state of an organic compound can be of two types: a singlet excited state and a triplet excited state. In addition, luminescence from the singlet excited state (S*) is referred to as fluorescence, and luminescence from the triplet excited state (T*) is referred to as phosphorescence. Furthermore, it is thought that the ratio of S* to T* in a light-emitting element is statistically 1:3.

At room temperature, a compound that converts a singlet excited state into luminescence (hereinafter referred to as a fluorescent compound) exhibits only luminescence from the singlet excited state (fluorescence), not luminescence from a triplet excited state (phosphorescence). On the basis that S*:T*=1:3, the internal quantum efficiency (ratio of generated photons to injected carriers) of a light-emitting element using a fluorescent compound is thought to have a theoretical limit of 25%.

However, with use of a compound that converts a triplet excited state into luminescence (hereinafter referred to as a phosphorescent compound), the internal quantum efficiency can theoretically be 75% to 100%. That is, the emission efficiency can be three to four times as high as that of a fluorescent compound. From that reason, in order to achieve a light-emitting element with high efficiency, a light-emitting element using a phosphorescent compound has been actively developed in recent years (e.g., see Non-Patent Document 1).

When the above-described phosphorescent compound is used in a light-emitting layer of a light-emitting element, in order to suppress concentration quenching of the phosphorescent compound or quenching due to triplet-triplet annihilation, the light-emitting layer is often formed so that the phosphorescent compound is dispersed in a matrix including another substance. In that case, a substance serving as a matrix is referred to as a host material, and a substance that is dispersed in a matrix, like a phosphorescent compound, is referred to as a guest material.

When a phosphorescent compound is used as a guest material, a host material is needed to have triplet excitation energy (an energy difference between a ground state and a triplet excited state) higher than the phosphorescent compound. It is known that CBP which is used as a host material in Non-Patent Document 1 has higher triplet excitation energy than a phosphorescent compound which exhibits emission of green to red light, and is widely used as a host material of the phosphorescent compound.

Despite the high triplet excitation energy, CBP is poor in ability to receive holes or electrons, which results in a problem in that driving voltage gets higher. In view of the above problem, a substance that has high triplet excitation energy and also can easily accept or transport both holes and electrons (i.e. a bipolar substance) is required as a host material of a phosphorescent compound.

Because singlet excitation energy (an energy difference between a ground state and a singlet excited state) is greater than triplet excitation energy, a material that has high triplet excitation energy will also have high singlet excitation energy. A bipolar substance having high triplet excitation energy is therefore also useful as a host material in a light-emitting element formed using a fluorescent compound as a light-emitting substance.

REFERENCE

Non-Patent Document

[Non-Patent Document 1] M. A. Baldo, etc., *Applied Physics Letters*, vol. 75, No. 1, pp. 4-6, 1999

SUMMARY OF THE INVENTION

An object of one embodiment of the present invention is to provide a substance that has high excitation energy, in particular, high triplet excitation energy.

In addition, another object of one embodiment of the present invention is to provide a bipolar substance.

Another object of one embodiment of the present invention is to provide a novel light-emitting substance.

Another object of one embodiment of the present invention is to improve element characteristics of a light-emitting element.

Another object of one embodiment of the present invention is to provide a display device or lighting device with low power consumption.

Another object of one embodiment of the present invention is to provide an electronic device with low power consumption.

One embodiment of the present invention is an oxadiazole derivative represented by General Formula (G1) below.

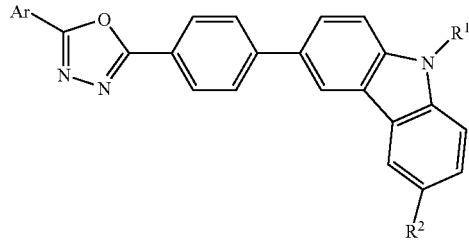
(G1)

In the formula, Ar represents a substituted or unsubstituted aryl group having 6 to 10 carbon atoms in a ring. $R^1$ represents an alkyl group having 1 to 4 carbon atoms or a substituted or unsubstituted aryl group having 6 to 10 carbon atoms in a ring. $R^2$ represents hydrogen, an alkyl group having 1 to 4 carbon atoms, or a substituted or unsubstituted aryl group having 6 to 10 carbon atoms in a ring.

In General Formula (G1), when at least one of Ar, $R^1$, and $R^2$ represents an aryl group having one or more substituents, the substituent(s) is an alkyl group having 1 to 4 carbon atoms or an aryl group having 6 to 10 carbon atoms in a ring.

Another embodiment of the present invention is an oxadiazole derivative represented by General Formula (G2) below.

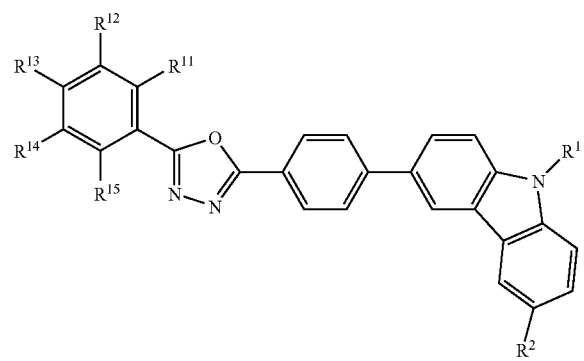
(G2)

In the formula, $R^1$ represents an alkyl group having 1 to 4 carbon atoms or a substituted or unsubstituted aryl group having 6 to 10 carbon atoms in a ring. $R^2$ represents hydrogen, an alkyl group having 1 to 4 carbon atoms, or a substituted or unsubstituted aryl group having 6 to 10 carbon atoms in a ring. $R^{11}$ to $R^{15}$ each represent hydrogen, an alkyl group having 1 to 4 carbon atoms, or an aryl group having 6 to 10 carbon atoms in a ring.

When at least either $R^1$ or $R^2$ represents an aryl group having one or more substituents, the substituent(s) is an alkyl group having 1 to 4 carbon atoms or an aryl group having 6 to 10 carbon atoms in a ring.

Another embodiment of the present invention is an oxadiazole derivative represented by General Formula (G3) below.

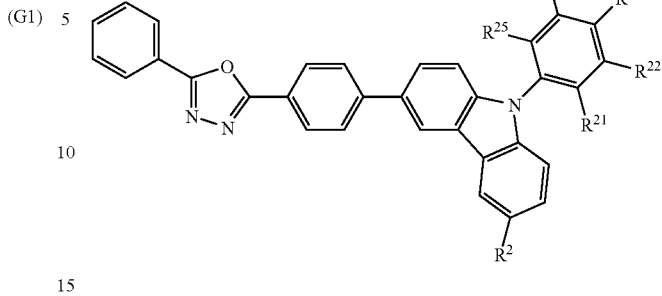
(G3)

In the formula, $R^2$ represents hydrogen, an alkyl group having 1 to 4 carbon atoms, or a substituted or unsubstituted aryl group having 6 to 10 carbon atoms in a ring. $R^{21}$ to $R^{25}$ each represent hydrogen, an alkyl group having 1 to 4 carbon atoms, or an aryl group having 6 to 10 carbon atoms in a ring.

When $R^2$ represents an aryl group having one or more substituents, the substituent(s) is an alkyl group having 1 to 4 carbon atoms or an aryl group having 6 to 10 carbon atoms in a ring.

Another embodiment of the present invention is an oxadiazole derivative represented by General Formula (G4) below.

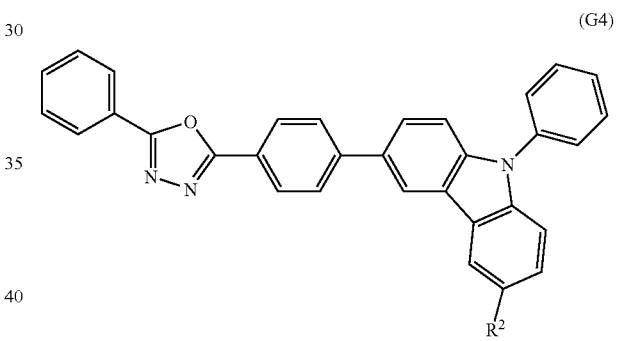
(G4)

In the formula, $R^2$ represents hydrogen, an alkyl group having 1 to 4 carbon atoms, or a substituted or unsubstituted aryl group having 6 to 10 carbon atoms in a ring.

When $R^2$ represents an aryl group having one or more substituents, the substituent(s) is an alkyl group having 1 to 4 carbon atoms or an aryl group having 6 to 10 carbon atoms in a ring.

Another embodiment of the present invention is a light-emitting element which has a light-emitting layer including any of the above-described oxadiazole derivatives.

Another embodiment of the present invention is a light-emitting element which has a light-emitting layer including any of the above-described oxadiazole derivatives and a light-emitting substance.

Another embodiment of the present invention is a light-emitting element which has a light-emitting layer including any of the above-described oxadiazole derivatives and a light-emitting layer including a phosphorescent compound.

Another embodiment of the present invention is a display device which has any of the above-described light-emitting elements and a controller of light emission from the light-emitting element. Note that the term "display device" in this specification means a device which individually controls light emission from a large number of light-emitting regions so that an image, movie, or the like can be displayed, and the display device functions as a visual object. In addition, the "display device" includes the following modules in its category: a module to which a connector such as a flexible printed circuit (FPC), a tape automated bonding (TAB) tape, or a tape carrier package (TCP) is attached; a module provided with a printed wiring board at the end of the TAB tape or the TCP; and a module in which an integrated circuit (IC) is directly mounted to a light-emitting element by a chip on glass (COG) method.

Another embodiment of the present invention is a lighting device which has any of the above-described light-emitting elements and a controller of light emission from the light-emitting element. Note that the term "lighting device" in this specification means a device which functions as a light source capable of continuously emitting light with a certain luminance and which aims to utilize light for a better human life. For example, with use of the device, a scene, a visual object, and the periphery thereof are lit up to be more recognizable or information is transmitted with a visual signal.

Another embodiment of the present invention is an electronic device which has any of the above-described light-emitting elements in a display portion or an illuminating portion. Note that the term "electronic device" in this specification means an electrical appliance to which an electronic engineering technique is applied, and examples thereof include the above-described display device and lighting device.

An oxadiazole derivative which is one embodiment of the present invention has an oxadiazole ring, thereby having high excitation energy, in particular, high triplet excitation energy.

In addition, the oxadiazole derivative which is one embodiment of the present invention has an oxadiazole ring having an electron-transport property and a carbazole ring having a hole-transport property, and consequently, the oxadiazole derivative is bipolar.

In addition, since the oxadiazole derivative which is one embodiment of the present invention has an energy gap of approximately 3.0 eV to 3.3 eV, the oxadiazole derivative is a novel fluorescent compound which emits blue light.

In addition, the oxadiazole derivative which is one embodiment of the present invention has high excitation energy, in particular, high triplet excitation energy, and is bipolar. As a result, in the case of using the oxadiazole derivative as a host material, electrons and holes are supplied to a light-emitting substance with a low driving voltage.

In addition, since a light-emitting element which is one embodiment of the present invention is formed using the bipolar oxadiazole derivative which has high excitation energy, in particular, high triplet excitation energy, the current efficiency of the light-emitting element can be increased. Note that examples of the light-emitting elements include the following: a light-emitting element to which the oxadiazole derivative is applied as a host material of a phosphorescent compound; a light-emitting element to which the oxadiazole derivative is applied as a host material of a fluorescent compound which emits blue light; a light-emitting element to which the oxadiazole derivative is applied as a light-emitting substance; and the like.

In addition, since a display device or a lighting device which is one embodiment of the present invention includes a light-emitting element with high current efficiency, the power consumption can be reduced.

In addition, since an electronic device which is one embodiment of the present invention includes the light-emitting element with high current efficiency in a display portion or illuminating portion, the power consumption can be reduced.

DETAILED DESCRIPTION OF THE INVENTION

Figure 1:
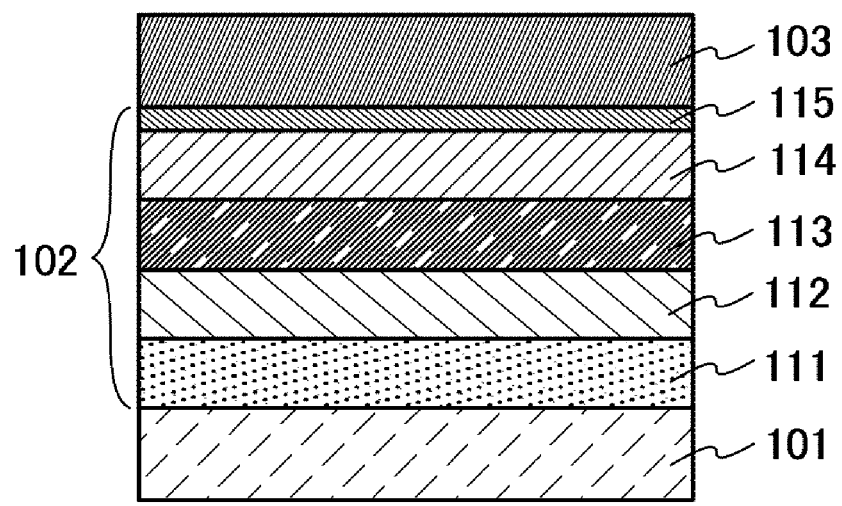
FIG. 1 illustrates a light-emitting element described in Embodiment 2.

Embodiments and examples of the present invention will be described in detail below with reference to the accompanying drawings. Note that the present invention is not limited to the description below, and it is easily understood by those skilled in the art that a variety of changes and modifications can be made without departing from the spirit and scope of the present invention. The present invention should therefore not be limited to the description of the embodiments and the examples below.

Embodiment 1

In this embodiment, described are oxadiazole derivatives which are one embodiment of the present invention and synthetic methods thereof.

The oxadiazole derivatives which are one embodiment of the present invention are represented by General Formulas (G1) to (G4).

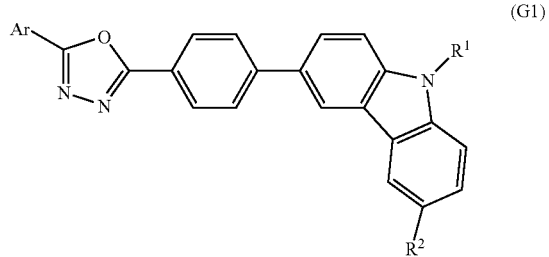
(G1)

In the formula, Ar represents a substituted or unsubstituted aryl group having 6 to 10 carbon atoms in a ring. $R^1$ represents an alkyl group having 1 to 4 carbon atoms or a substituted or unsubstituted aryl group having 6 to 10 carbon atoms in a ring. $R^2$ represents hydrogen, an alkyl group having 1 to 4 carbon atoms, or a substituted or unsubstituted aryl group having 6 to 10 carbon atoms in a ring.

In General Formula (G1), when at least one of Ar, $R^1$, and $R^2$ represent an aryl group having one or more substituents, the substituent(s) is an alkyl group having 1 to 4 carbon atoms or an aryl group having 6 to 10 carbon atoms in a ring.

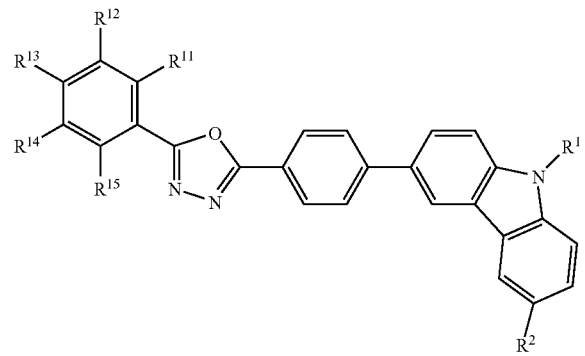
(G2)

In the formula, $R^1$ represents an alkyl group having 1 to 4 carbon atoms or a substituted or unsubstituted aryl group having 6 to 10 carbon atoms in a ring. $R^2$ represents hydrogen, an alkyl group having 1 to 4 carbon atoms, or a substituted or unsubstituted aryl group having 6 to 10 carbon atoms in a ring. $R^{11}$ to $R^{15}$ each represent hydrogen, an alkyl group having 1 to 4 carbon atoms, or an aryl group having 6 to 10 carbon atoms in a ring.

In General Formula (G2), when at least either $R^1$ or $R^2$ represents an aryl group having one or more substituents, the substituent(s) is an alkyl group having 1 to 4 carbon atoms or an aryl group having 6 to 10 carbon atoms in a ring.

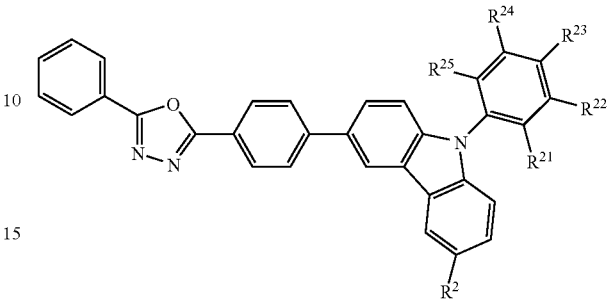
(G3)

In the formula, $R^2$ represents hydrogen, an alkyl group having 1 to 4 carbon atoms, or a substituted or unsubstituted aryl group having 6 to 10 carbon atoms in a ring. $R^{21}$ to $R^{25}$ each represent hydrogen, an alkyl group having 1 to 4 carbon atoms, or an aryl group having 6 to 10 carbon atoms in a ring.

In General Formula (G3), when $R^2$ represents an aryl group having one or more substituents, the substituent(s) is an alkyl group having 1 to 4 carbon atoms or an aryl group having 6 to 10 carbon atoms in a ring.

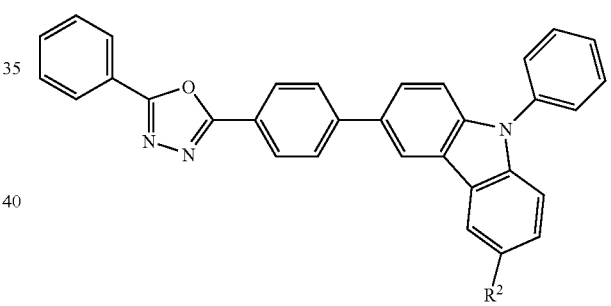
(G4)

In the formula, $R^2$ represents hydrogen, an alkyl group having 1 to 4 carbon atoms, or a substituted or unsubstituted aryl group having 6 to 10 carbon atoms in a ring.

In General Formula (G4), when $R^2$ represents an aryl group having one or more substituents, the substituent(s) is an alkyl group having 1 to 4 carbon atoms or an aryl group having 6 to 10 carbon atoms in a ring.

Specifically, Ar, $R^1$, and $R^2$ in General Formulas (G1) to (G4) can be substituents represented by Structural Formulas (1-1) to (1-17).

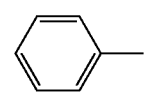
(1-1)

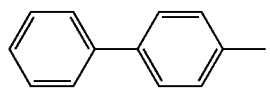
(1-2)

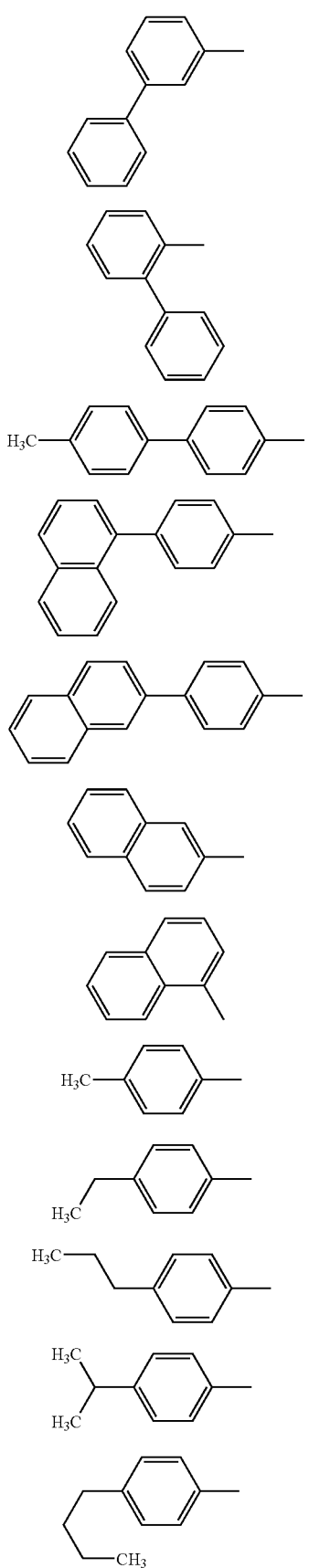
(1-3) 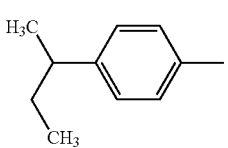
(1-4) 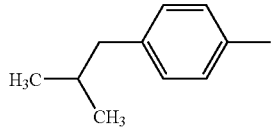
(1-5) 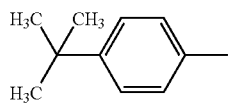
In addition, R¹ and R² in General Formulas (G1) to (G4) can also be substituents represented by Structural Formulas (2-1) to (2-8).
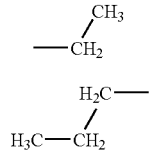
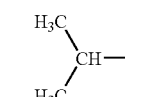
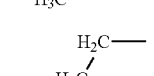
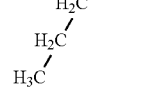
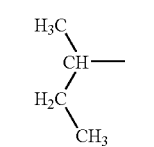
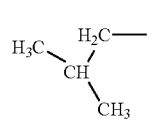
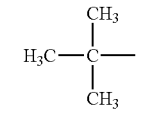
Further, R² in General Formulas (G1) to (G4) can also be a substituent represented by Structural Formula (3-1).
H—          (3-1)

Specifically, $R^{11}$ to $R^{15}$ in General Formula (G2), and $R^{21}$ to $R^{25}$ in General Formula (G3) can be substituents represented by Structural Formulas (4-1) to (4-20).
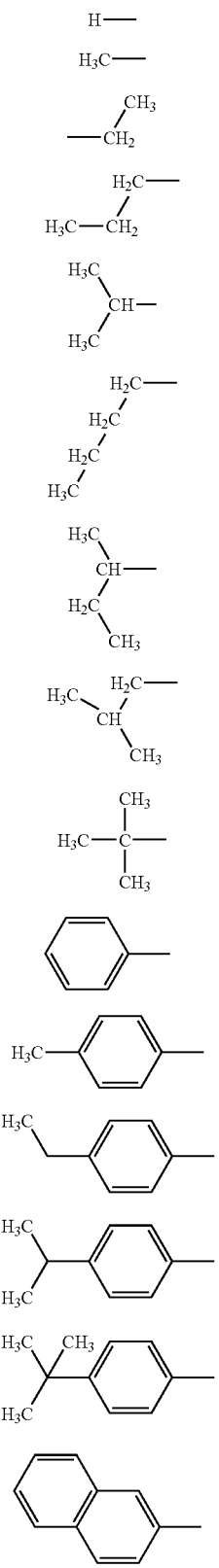
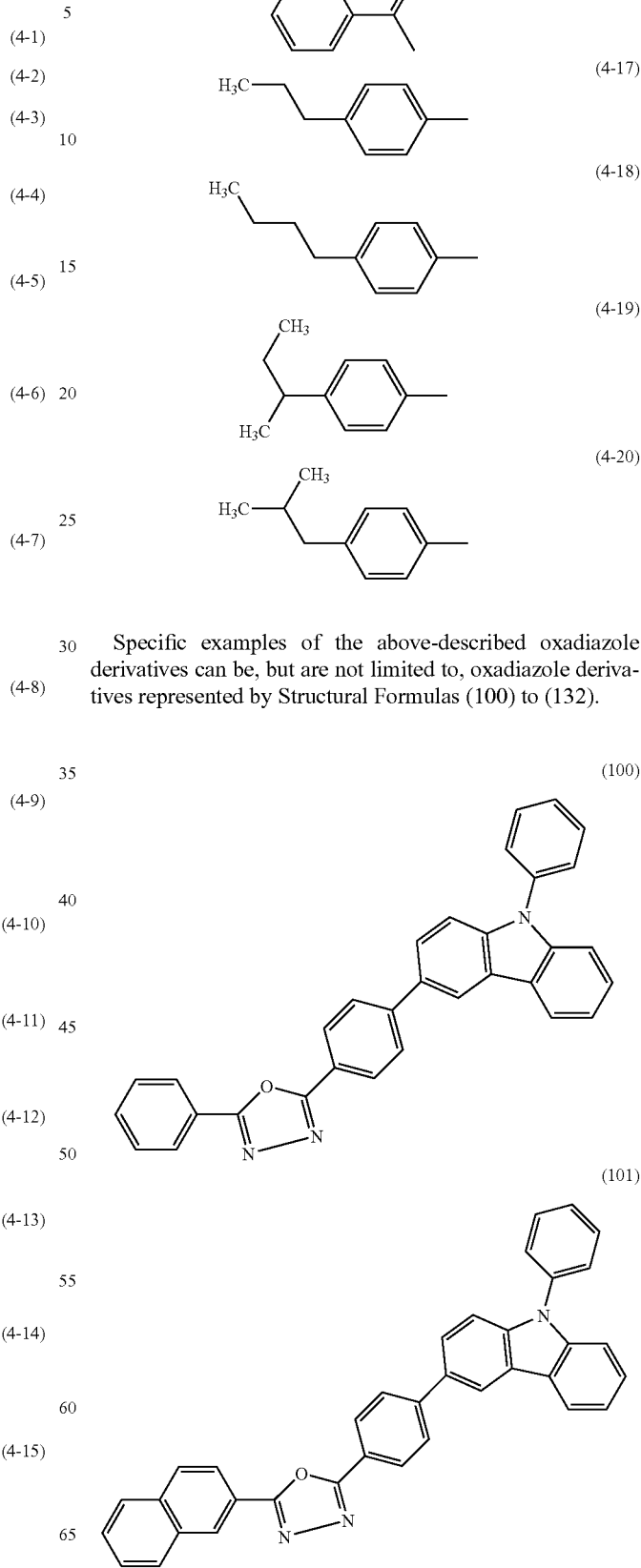
Specific examples of the above-described oxadiazole derivatives can be, but are not limited to, oxadiazole derivatives represented by Structural Formulas (100) to (132).

(102)
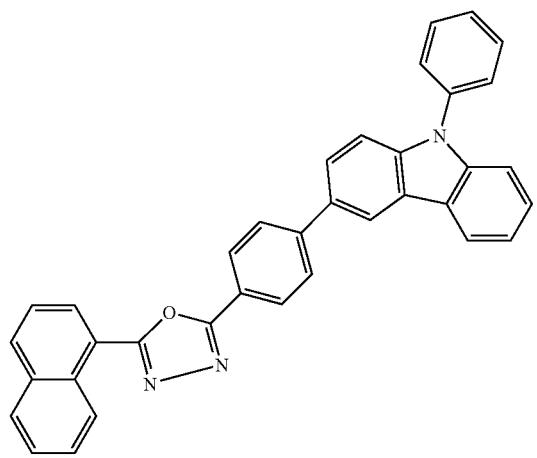
(103)
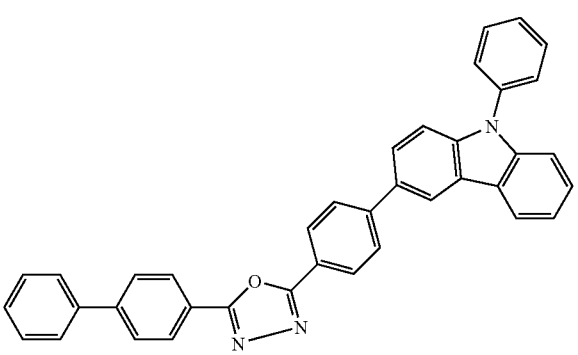
(104)
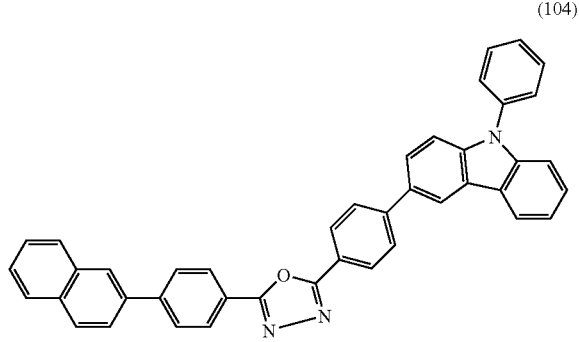
(105)
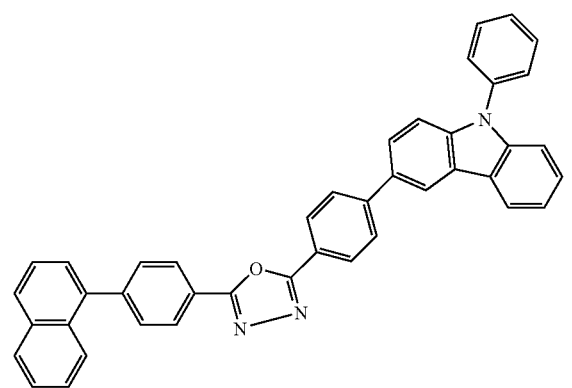
(106)
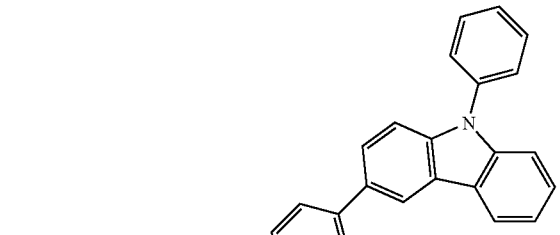
(107)
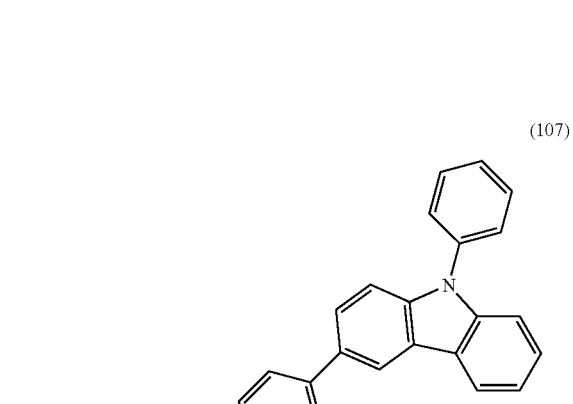
(108)
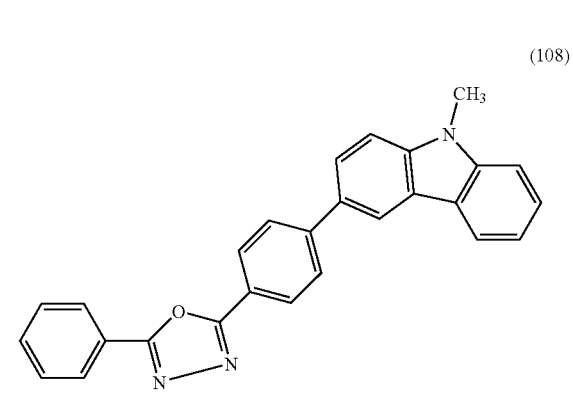

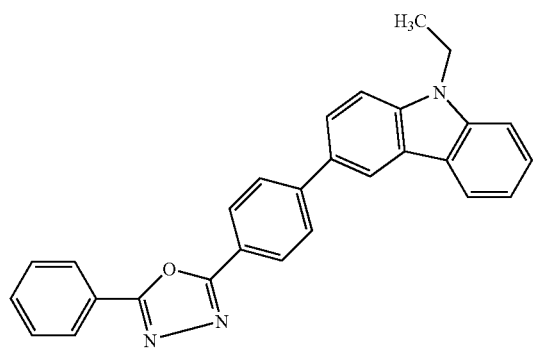
(109)
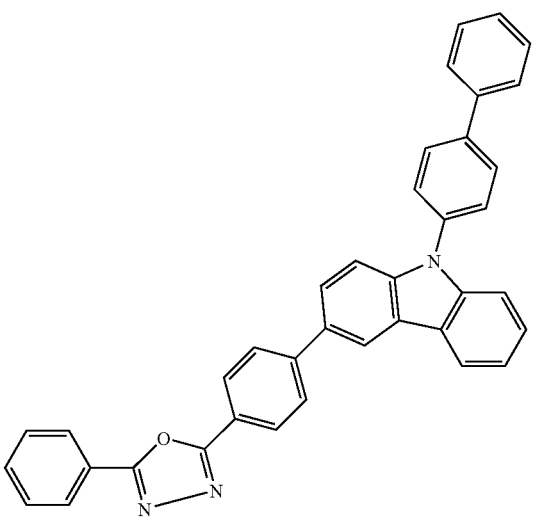
(112)
(110)
(113)
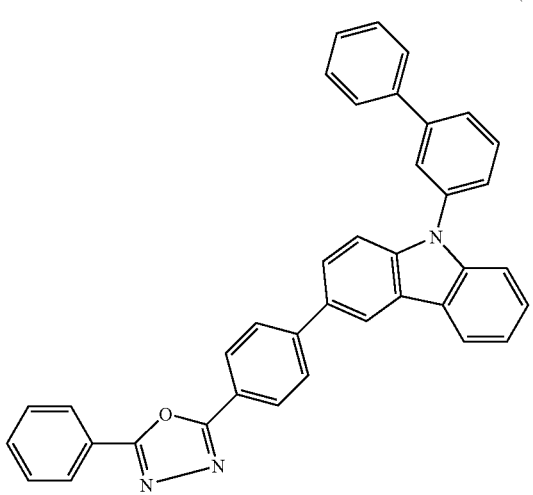
(111)
(114)
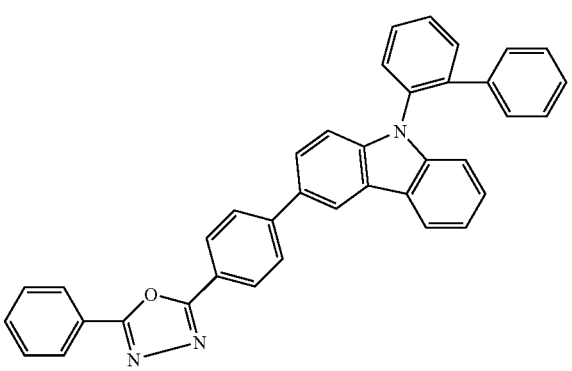

(115)
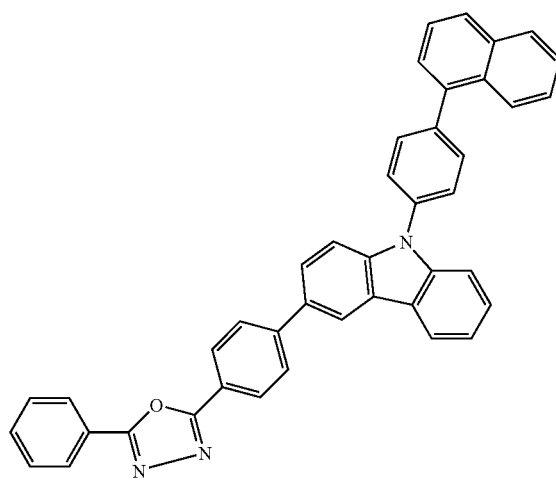
(116)
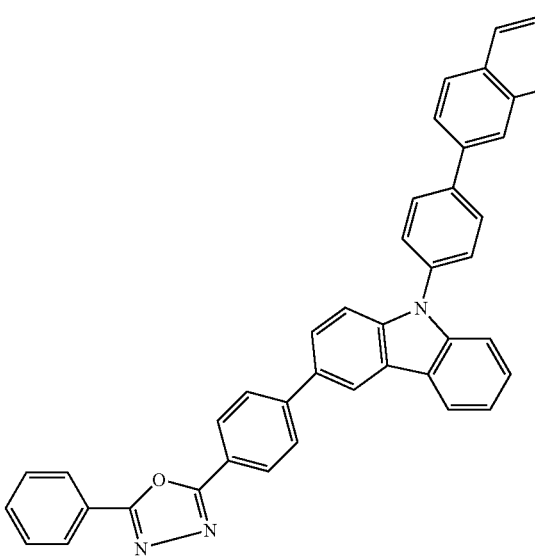
(117)
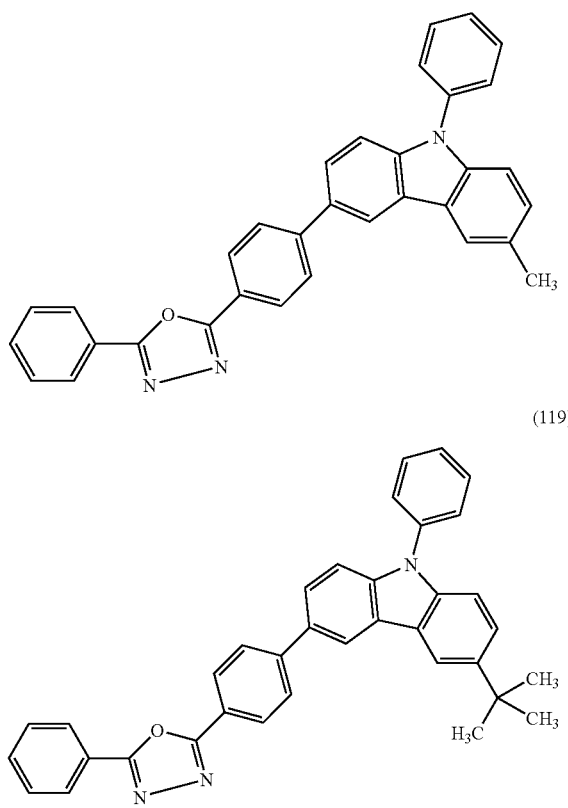
(118)
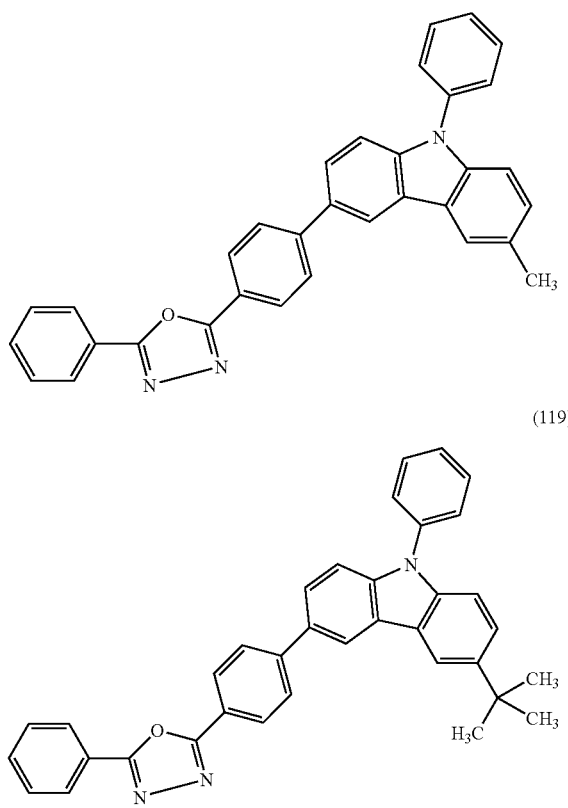
(119)
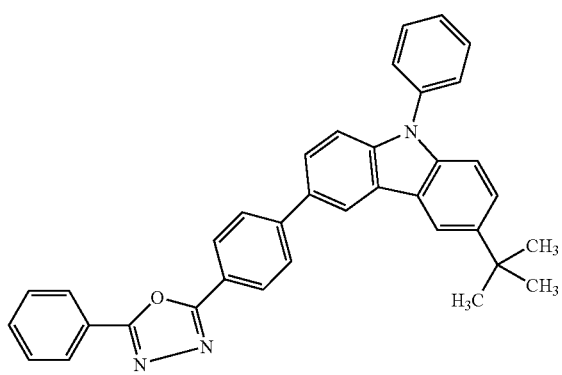
(120)
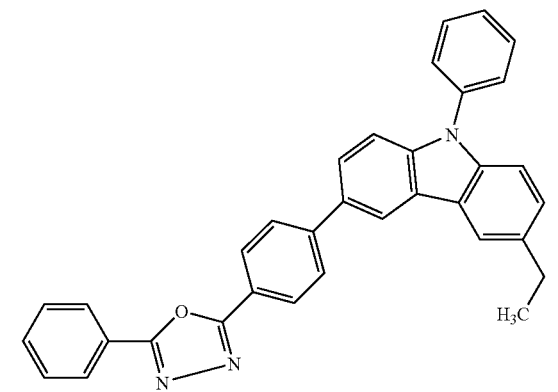
(121)
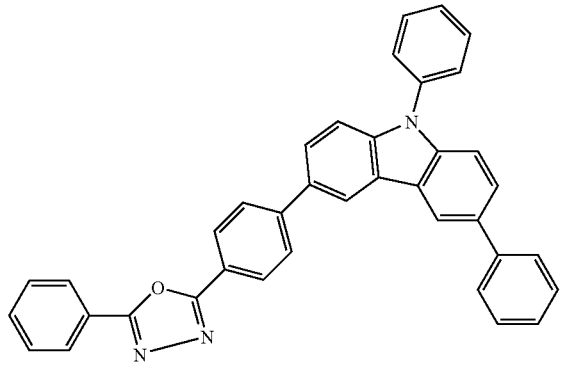

(122)
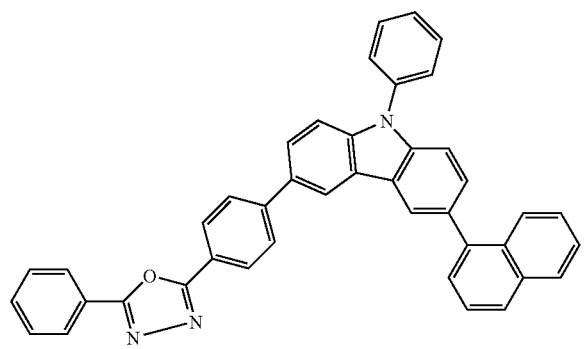
(123)
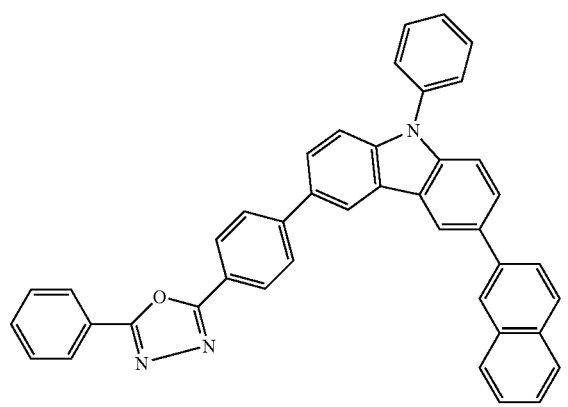
(124)
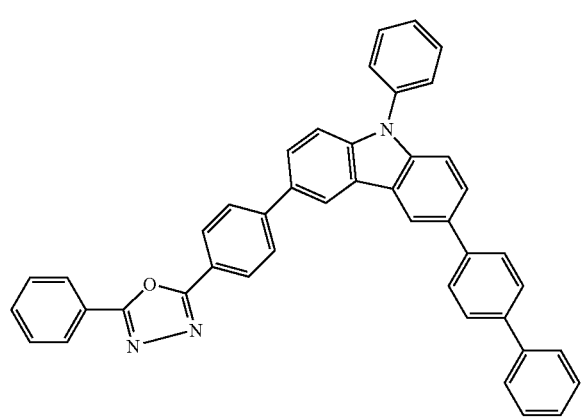
(125)
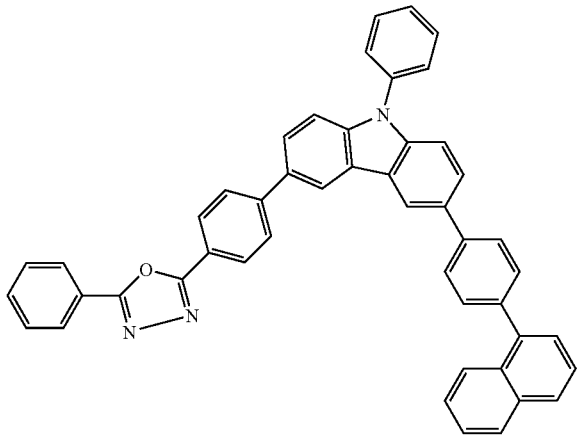
(126)
(127)
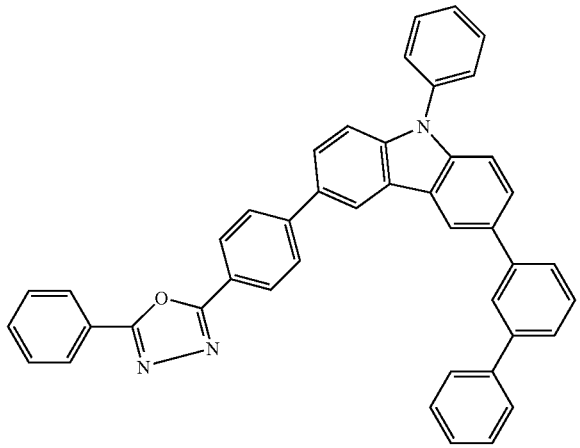

(128)

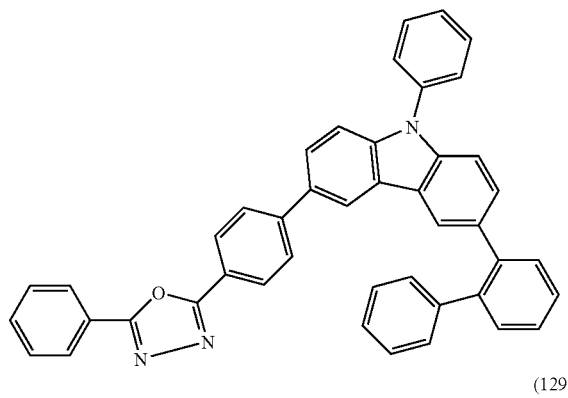

(129)

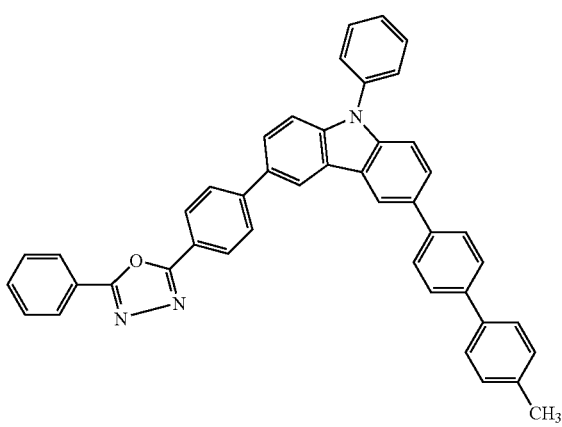

(130)

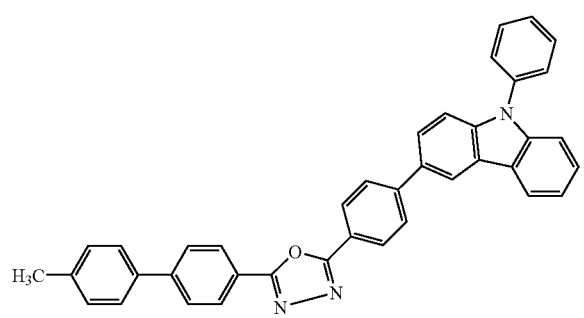

(131)

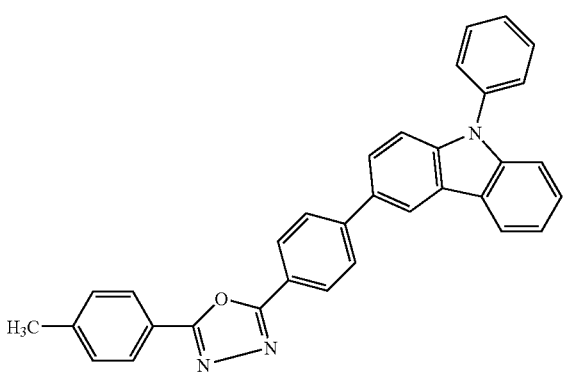

(132)

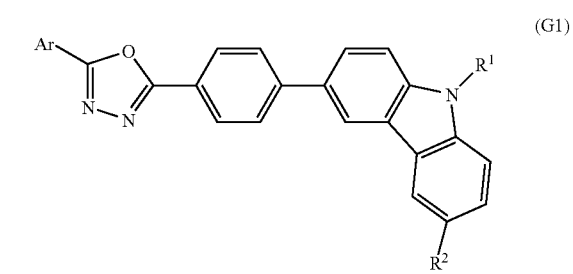

The oxadiazole derivatives of one embodiment of the present invention can be synthesized by applying various reactions. For example, a synthesis reaction described below can be performed so as to synthesize one of the oxadiazole derivatives of one embodiment of the present invention which is represented by General Formula (G1) below. Note that the synthesis method of the oxadiazole derivative of one embodiment of the present invention is not limited to the synthesis method below.

(G1)

<Method 1 for Synthesizing Oxadiazole Derivative Represented by General Formula (G1)>

The oxadiazole derivative represented by General Formula (G1) can be synthesized through the Suzuki-Miyaura reaction in Synthetic Scheme (A-1) below. Specifically, the oxadiazole derivative represented by General Formula (G1) can be obtained by coupling a halogenated oxadiazole compound (Compound A1) and a 9H-carbazole-3-boronic acid derivative (Compound B1) using a palladium catalyst in the presence of a base.

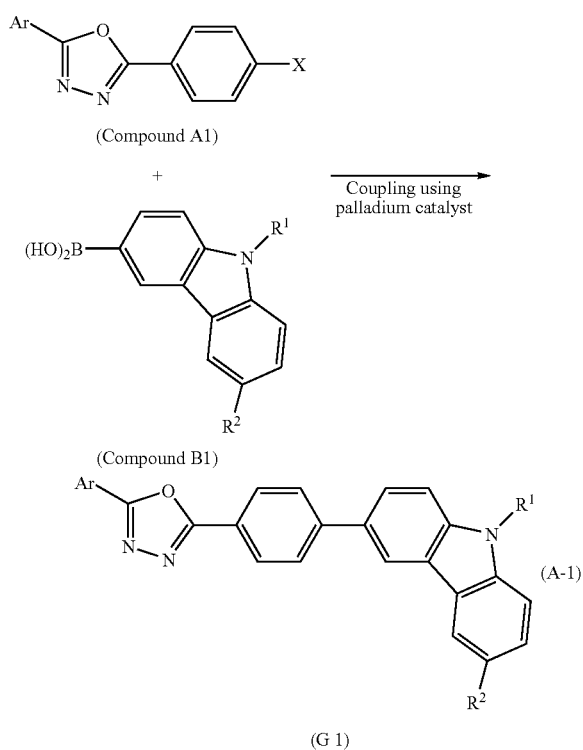

(G 1)

The halogenated oxadiazole derivative (Compound A1) is an oxadiazole derivative in which X in the formula is a halogen. Note that the halogen is preferably a highly-reactive element such as bromine or iodine.

In the formula, Ar represents a substituted or unsubstituted aryl group having 6 to 10 carbon atoms in a ring. $R^1$ represents an alkyl group having 1 to 4 carbon atoms or a substituted or unsubstituted aryl group having 6 to 10 carbon atoms in a ring. $R^2$ represents hydrogen, an alkyl group having 1 to 4 carbon atoms, or a substituted or unsubstituted aryl group having 6 to 10 carbon atoms in a ring. When at least one of Ar, $R^1$, and $R^2$ represents an aryl group having one or more substituents, the substituent(s) is an alkyl group having 1 to 4 carbon atoms or an aryl group having 6 to 10 carbon atoms in a ring.

Examples of the palladium catalyst which can be used in the Suzuki-Miyaura reaction in Synthesis Scheme (A-1) include palladium(II) acetate, tetrakis(triphenylphosphine)palladium(0), and the like. Note that examples of ligands of the palladium catalysts which can be used in Synthesis Scheme (A-1) include tri(o-tolyl)phosphine, triphenylphosphine, tricyclohexylphosphine, and the like.

Examples of the base which can be used in the Suzuki-Miyaura reaction in Synthesis Scheme (A-1) include an organic base such as sodium tert-butoxide, an inorganic base such as potassium carbonate, and the like.

Examples of a solvent which can be used in the Suzuki-Miyaura reaction in Synthesis Scheme (A-1) include the following: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane and water; and the like. In particular, use of a mixed solvent of toluene and water or a mixed solvent of toluene, ethanol, and water is preferable.

The oxadiazole derivatives represented by General Formulas (G2) to (G4) can be synthesized through a reaction similar to that described above. That is, the oxadiazole derivatives represented by General Formulas (G2) to (G4) can be obtained by coupling a halogenated oxadiazole derivative in which Ar is substituted as appropriate and a carbazole derivative in which $R^1$ is substituted as appropriate.

Each of the oxadiazole derivatives described in this embodiment has an oxadiazole ring, thereby having high excitation energy, in particular, high triplet excitation energy.

Each of the oxadiazole derivatives described in this embodiment has an oxadiazole ring having an electron-transport property and a carbazole ring having a hole-transport property, and consequently, the oxadiazole derivative is bipolar.

Embodiment 2

In this embodiment, described is a light-emitting element in which any of the oxadiazole derivatives of one embodiment of the present invention is used for a light-emitting layer, with reference to FIG. 1.

FIG. 1 illustrates an example of a light-emitting element in which an EL layer 102 including a light-emitting layer 113 is interposed between a first electrode 101 and a second electrode 103. The light-emitting layer 113 includes any of the oxadiazole derivatives described in Embodiment 1.

By applying voltage between the first electrode 101 and the second electrode 103, holes are injected from the first electrode 101 side and electrons are injected from the second electrode 103 side to recombine in the light-emitting layer 113, and a substance in the light-emitting layer 113 is raised to an excited state. After that, the substance in the excited state emits light in relaxation to the ground state. Note that in the light-emitting element described in this embodiment, the first electrode 101 and the second electrode 103 function as an anode and a cathode, respectively.

The first electrode 101 functioning as an anode is preferably formed using a metal, an alloy, an electrically conductive compound, a mixture thereof, or the like which has a high work function (specifically, 4.0 eV or higher). Specific examples include indium oxide-tin oxide (ITO: indium tin oxide), indium oxide-tin oxide containing silicon or silicon oxide, indium oxide-zinc oxide (IZO: indium zinc oxide), and indium oxide containing tungsten oxide and zinc oxide, and the like. In addition to these substances, there are gold (Au), platinum (Pt), nickel (Ni), tungsten (W), chromium (Cr), molybdenum (Mo), iron (Fe), cobalt (Co), copper (Cu), palladium (Pd), titanium (Ti), and the like.

Note that, when a layer in contact with the first electrode 101 included in the EL layer 102 is formed using a composite material in which an organic compound and an electron acceptor which are described later are mixed, the first electrode 101 can be formed using any of various types of metals, alloys, and electrically-conductive compounds, a mixture thereof, and the like regardless of a value of the work function. For example, aluminum (Al), silver (Ag), an alloy including aluminum (e.g., AlSi), or the like can also be used.

Note that the first electrode 101 can be formed by, for example, a sputtering method, an evaporation method (including a vacuum evaporation method), or the like.

The EL layer 102 formed over the first electrode 101 has at least the light-emitting layer 113 and is formed to include any of the oxadiazole derivatives described in Embodiment 1. The EL layer 102 can also partially include a known substance, for which either a low molecular compound or a high molecular compound may be used. Note that the substance used for forming the EL layer 102 may have not only a structure formed of only an organic compound but also a structure in which an inorganic compound is partially contained.

Further, as illustrated in FIG. 1, the EL layer 102 includes the light-emitting layer 113 and also the following layers stacked in appropriate combination: a hole-injection layer 111 including a substance having a high hole-injection property, a hole-transport layer 112 including a substance having a high hole-transport property, an electron-transport layer 114 including a substance having a high electron-transport property, an electron-injection layer 115 including a substance having a high electron-injection property, and the like.

The hole-injection layer 111 includes a substance having a high hole-injection property. As the substance having a high hole-injection property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Further, it is possible to use aromatic amine compounds, which are low molecular organic compounds, as follows: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Further alternatively, high molecular compounds (e.g., oligomers, dendrimers, or polymers) can be used. Examples of the high molecular compounds include the following: poly (N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Alternatively, for the hole-injection layer 111, a composite material formed by combining an organic compound and an electron acceptor may be used. Such a composite material has excellent hole-injection and -transport properties because the electron acceptor produces holes in the organic compound. In this case, as the organic compound, a material that can efficiently transport the produced holes (a substance having a high hole-transport property) is preferably used.

As the organic compound for the composite material, various compounds such as an aromatic amine compound, carbazole derivatives, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ $cm^2/Vs$ or higher is preferably used. However, substances other than the above-described materials may also be used as long as the substances have higher hole-transport properties than electron-transport properties. The organic compounds which can be used for the composite material will be specifically given below.

Examples of the organic compounds that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD) and N,N'-bis(3-methylphenyl)-N,N'-diphenyl-[1,1'-biphenyl]-4,4'-diamine (abbreviation: TPD) and carbazole derivatives such as 4,4'-di(N-carbazolyl)biphenyl (abbreviation: CBP), 1,3,5-tris[4-(N-carbazolyl)-phenyl]benzene (abbreviation: TCPB), 9-[4-(N-carbazolyl)]phenyl-10-phenylanthracene (abbreviation: CzPA), and 1,4-bis[4-(N-carbazolyl)phenyl-2,3,5,6-tetraphenylbenzene.

In addition, it is possible to use the following aromatic hydrocarbon compounds: 2-tert-butyl-9,10-di(2-naphthyl) anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di (2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis [2-(1-naphthyl)phenyl]anthracene, 2,3,6,7-tetramethyl-9,10-di(1-naphthyl)anthracene, or the like.

Further, it is also possible to use the following aromatic hydrocarbon compounds: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, and 9,10-bis[4-(2,2-diphenylvinyl)phenyl]anthracene (abbreviation: DPVPA).

Further, as examples of electron acceptors that can be used for the composite material, there are organic compounds such as 7,7,8,8-tetracyano-2,3,5,6-tetrafluoroquinodimethane (abbreviation: $F_4$-TCNQ) and chloranil, transition metal oxides, and the like. In addition, oxides of metals belonging to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these substances, molybdenum oxide is especially preferable because of stability in air and a low hygroscopic property so as to be easily treated.

Note that a composite material formed using any of the above-mentioned high molecular compounds such as PVK, PVTPA, PTPDMA, and Poly-TPD and any of the above-mentioned electron acceptors may be used for the hole-injection layer 111.

The hole-transport layer 112 includes a substance having a high hole-transport property. As a substance having a high hole-transport property, there are aromatic amine compounds such as NPB, TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). Most of the substances mentioned here have a hole mobility of $10^{-6}$ $cm^2/Vs$ or more. Note that the layer which contains a substance having a high hole-transport property is not limited to a single layer, and two or more layers containing the above substances may be stacked.

Further alternatively, for the hole-transport layer 112, a high molecular compound such as PVK, PVTPA, PTPDMA, or Poly-TPD can be used.

In the light-emitting layer 113, any of the oxadiazole derivatives described in Embodiment 1 is used as a matrix (a host material), and in the matrix, there is a substance having a high light-emitting property (a guest material) dispersed.

In the case of using a fluorescent compound as the guest material, it is preferred that the lowest unoccupied molecular orbital level (LUMO level) be lower than those of the oxadiazole derivatives described in Embodiment 1 and that the highest occupied molecular orbital level (HOMO level) of the fluorescent compound be higher than those of the oxadiazole derivatives described in Embodiment 1. Examples of the fluorescent compounds include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phen ylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetramine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

In the case of using a phosphorescent compound as the guest material, it is preferred that the triplet-excitation energy of the phosphorescent compound be lower than that of the oxadiazole derivatives described in Embodiment 1. Examples include organometallic complexes such as bis[2-(3',5'-bistrifluoromethylphenyl)pyridinato-N,C$^{2'}$]iridium(III)picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), tris(2-phenylpyridinato-N,C$^{2'}$)iridium(III) (abbreviation: Ir(ppy)$_3$), bis(2-phenylpyridinato)iridium(III) acetylacetonato (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), bis[2-(2'-benzo[4,5-a]thienyl)pyridinato-N,C$^{3'}$](III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

Since the oxadiazole derivatives described in Embodiment 1 are bipolar, with use of any of them for a host material of the light-emitting layer 113, a light-emitting layer with a high carrier-transport property can be obtained.

The substance (the host material) for dispersion of the light-emitting substance (the guest material) can be a plurality of kinds of substances. The light-emitting layer 113 therefore may include a second host material in addition to any of the oxadiazole derivatives described in Embodiment 1.

Although the light-emitting element to which any of the oxadiazole derivatives described in Embodiment 1 is applied as the host material is described here, the oxadiazole derivatives can also be used as the light-emitting substance (the guest material).

The electron-transport layer 114 includes a substance having a high electron-transport property. The electron-transport layer 114 can be formed using a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), or bis[2-(2-hydroxyphenyl)benzothiazolato]zinc (abbreviation: Zn(BTZ)$_2$). Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. Most of the substances mentioned here have an electron mobility of $10^{-6}$ $cm^2/Vs$ or more.

Note that the electron-transport layer is not limited to a single layer, and two or more layers containing the above substances may be stacked.

The electron-injection layer 115 includes a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide ($LiO_x$) can be used. Alternatively, a rare earth metal compound such as erbium fluoride ($ErF_3$) can also be used. Further alternatively, any of the above-described substances that are used to form the electron-transport layer 114 may be used.

For the electron-injection layer 115, a composite material formed by combining an organic compound and an electron donor may also be used. Such a composite material has excellent electron-injection and -transport properties because the electron donor produces electrons in the organic compound. In this case, as the organic compound, a material that can efficiently transport the produced electrons is preferably used; for example, any of the above-described substances (e.g., a metal complex or a heteroaromatic compound) that are used to form the electron-transport layer 114 can be used. As the electron donor, a substance exhibiting an electron-donating property to the organic compound is used. Specifically, it is preferable to use any of alkali metals, alkali earth metals, or rare earth metals, such as lithium, cesium, magnesium, calcium, erbium, ytterbium, or the like. Alternatively, it is preferable to use any of alkali metal oxides or alkaline earth metal oxides: lithium oxide, calcium oxide, barium oxide, or the like. A Lewis base such as magnesium oxide can also be used. Alternatively, an organic compound such as tetrathiafulvalene (abbreviation: TTF) can be used.

Note that the hole-injection layer 111, hole-transport layer 112, light-emitting layer 113, electron-transport layer 114, and electron-injection layer 115 which are described above can each be formed by an evaporation method (including a vacuum evaporation method), an inkjet method, a coating method, or the like.

The second electrode 103 functioning as a cathode is preferably formed using a metal, an alloy, an electrically conductive compound, a mixture thereof, or the like which has a low work function (preferably 3.8 eV or lower), or the like. Specific examples include elements that belong to Group 1 or Group 2 of the periodic table, that is, alkali metals such as lithium (Li) and cesium (Cs) or alkaline earth metals such as magnesium (Mg), calcium (Ca), and strontium (Sr), or alloys thereof (e.g., MgAg and AlLi); rare earth metals such as europium (Eu) and ytterbium (Yb), or alloys thereof; aluminum (Al); silver (Ag); and the like.

Note that, when a layer in contact with the second electrode 103 which is included in the EL layer 102 is formed using the above-described composite material of the organic compound and the electron donor, a material used for the second electrode 103 can be selected without being limited by the value of the work function. For example, any of a variety of conductive materials such as aluminum (Al), silver (Ag), ITO, and indium oxide-tin oxide containing silicon or silicon oxide can be used.

In the formation of the second electrode 103, a vacuum evaporation method or a sputtering method can be used. Alternatively, when a silver paste or the like is used, a coating method, an inkjet method, or the like may be used.

In the above-described light-emitting element, current flows due to a potential difference generated between the first electrode 101 and the second electrode 103, and holes and electrons recombine in the EL layer 102, whereby light is emitted. This emitted light is extracted out through either or both the first electrode 101 or/and the second electrode 103, or both. For that purpose, either or both the first electrode 101 or the second electrode 103 or both has/have a light-transmitting property.

Note that with the use of the light-emitting element described in this embodiment, a passive-matrix display device or an active-matrix display device in which drive of the light-emitting element is controlled by a thin film transistor (TFT) can be fabricated.

Note that there is no particular limitation on the structure of the TFT in the case of fabricating an active-matrix display device. For example, a staggered TFT or an inverted staggered TFT can be used as appropriate. Further, a driver circuit formed over a TFT substrate may be formed using both an n-type TFT and a p-type TFT or only either an n-type TFT or a p-type TFT. Furthermore, there is no particular limitation on materials of a semiconductor film used for the TFT. For example, a semiconductor film or an oxide semiconductor film formed using a Group 14 element of the periodic table, such as silicon or germanium can be used. Similarly, there is no particular limitation on the crystallinity of a semiconductor film used for the TFT. For example, either an amorphous semiconductor film or a crystalline semiconductor film may be used.

Since the light-emitting element described in this embodiment has the light-emitting layer 113 formed using any of the oxadiazole derivatives of Embodiment 1 which are bipolar substances, element efficiency such as current efficiency can be improved.

Although in this embodiment, the light-emitting element having the light-emitting layer formed using any of the oxadiazole derivatives described in Embodiment 1 is described, structures of the light-emitting element formed using any of the oxadiazole derivatives are not limited to the above description. For example, the bipolar oxadiazole derivatives can also be applied to a hole-transport layer or an electron-transport layer; therefore, a light-emitting element formed using any of the oxadiazole derivatives in the hole-transport layer or the electron-transport layer is also one embodiment of the present invention. Similarly, the bipolar oxadiazole derivatives can also be applied as an organic compound in a hole-injection layer which is formed by mixing the organic compound and an electron accepter, or as an organic compound in an electron-injection layer which is formed by mixing the organic compound and an electron donor; therefore, a light-emitting element formed using any of the oxadiazole derivatives as the organic compound in the hole-injection layer or the electron-injection layer is also one embodiment of the present invention.

Embodiment 3

Figure 2:
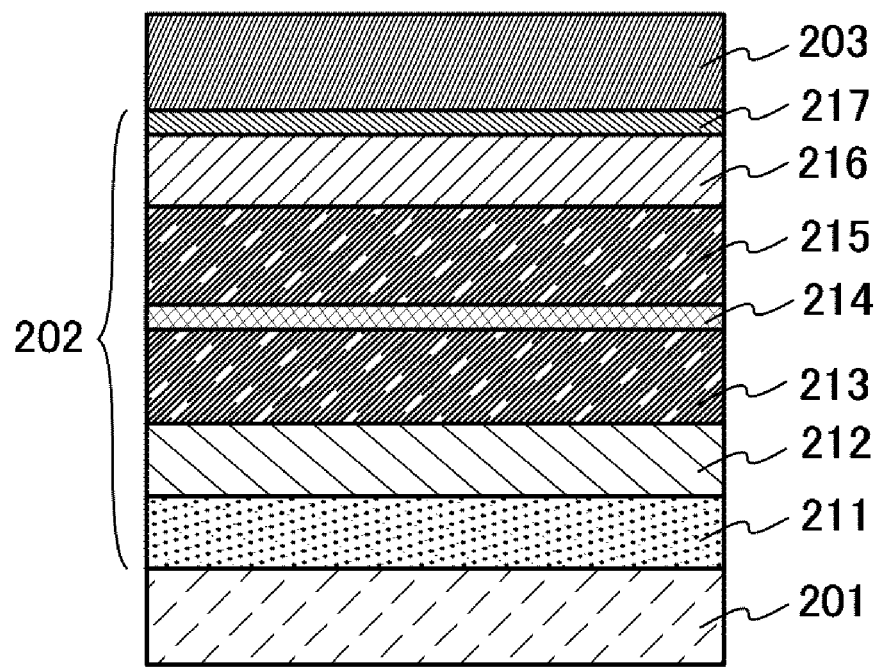
FIG. 2 illustrates a light-emitting element described in Embodiment 3.

In this embodiment, described is a light-emitting element including a plurality of light-emitting layers, with reference to FIG. 2. Specifically, described is a light-emitting element in which a plurality of light-emitting layers which emit light of wavelengths different from each other so that mixed light of the different colors can be emitted.

The light-emitting element in FIG. 2 is provided with an EL layer 202 including a first light-emitting layer 213 and a second light-emitting layer 215 between a first electrode 201 and a second electrode 203. The light-emitting element emits mixed light emitted from the first light-emitting layer 213 and the second light-emitting layer 215. A separation layer 214 is preferably provided between the first light-emitting layer 213 and the second light-emitting layer 215.

By application of voltage such that the potential of the first electrode 201 is higher than that of the second electrode 203, current flows between the first electrode 201 and the second electrode 203, and holes and electrons recombine in the first light-emitting layer 213, the second light-emitting layer 215, or the separation layer 214. The energy generated by the recombination is provided for both the first light-emitting layer 213 and the second light-emitting layer 215 so as to allow a first light-emitting substance included in the first light-emitting layer 213 and a second light-emitting substance included in the second light-emitting layer 215 to be excited. After that, the first and second light-emitting substances in the excited state emit light in relaxation to the ground state.

The first light-emitting layer 213 includes the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)galliumchloride (abbreviation: Gamq$_2$Cl) or a phosphorescent compound such as bis{2-[3,5-bis(trifluoromethyl)phenyl]pyridinato-N,C$^{2'}$}iridium(III) picolinate (abbreviation: Ir(CF$_3$ ppy)$_2$(pic)), bis[2-(4,6-difluorophenyl)pyridinato-N,C$^{2'}$]iridium(III) acetylacetonate (abbreviation: FIr(acac)), bis[2-(4,6-difluorophenyl)pyridinato-N,C$^{2'}$]iridium(III) picolinate (abbreviation: FIrpic), or bis[2-(4,6-difluorophenyl)pyridinato-N,C$^{2'}$]iridium(III) tetra (1-pyrazolyl)borate (abbreviation: FIr6), from which light emission with a peak at 450 nm to 510 nm in an emission spectrum (i.e., blue light to blue green light) can be obtained.

When a fluorescent compound is used as the first light-emitting substance, the first light-emitting layer 213 preferably has a structure in which a substance having larger singlet excited energy than the first light-emitting substance is used as a first host material and the first light-emitting substance is dispersed as a guest material. Alternatively, when a phosphorescent compound is used as the first light-emitting substance, the first light-emitting layer 213 preferably has a structure in which a substance having larger triplet excited energy than the first light-emitting substance is used as a first host material and the first light-emitting substance is dispersed as a guest material. The first host material can be NPB, CBP, TCTA, or the like, which is described above, or DNA, t-BuDNA, or the like. Note that the singlet excitation energy refers to an energy difference between a ground state and a singlet excited state. In addition, the triplet excitation energy refers to an energy difference between a ground state and a triplet excited state.

Further, the second light-emitting layer 215 includes any of the oxadiazole derivatives described in Embodiment 1 as a host material. The specific structure of the second light-emitting layer 215 is similar to that of the light-emitting layer 113 which is described in Embodiment 2.

In addition, the separation layer 214 can be formed using TPAQn, NPB, CBP, TCTA, Znpp$_2$, ZnBOX or the like described above. Provision of such a separation layer 214 can prevent an undesirable increase in the emission intensity of only either the first light-emitting layer 213 or the second light-emitting layer 215. Note that the separation layer 214 is not a necessary component. For example, the separation layer 214 may be provided as appropriate in order to adjust the ratio of the emission intensity of the first light-emitting layer 213 to that of the second light-emitting layer 215.

In this embodiment, the second light-emitting layer 215 is formed using a light-emitting layer in which any of the oxadiazole derivatives described in Embodiment 1 is used as a host material, and the first light-emitting layer 213 is formed using a light-emitting layer in which another material is used as a host material. In contrast, it is possible to form the first light-emitting layer 213 using the light-emitting layer in which any of the oxadiazole derivatives described in Embodiment 1 is used as a host material, and to form the second light-emitting layer 215 using the light-emitting layer in which another substance is used as a host material.

Further, the light-emitting element in which two light-emitting layers are provided as illustrated in FIG. 2 is described in this embodiment; however, the number of the light-emitting layers is not limited to two, and may be three, for example. In addition, light emission from each light-emitting layer may be mixed. For example, as a result of mixing two (or three) complementary colors, white light emission can be obtained. Note that "complementary colors" refer to colors that can produce an achromatic color when mixed.

Note that the first electrode 201 may have a structure similar to that of the first electrode 101 described in Embodiment 2. In addition, the second electrode 203 may also have a structure similar to that of the second electrode 103 described in Embodiment 2.

Further, in this embodiment, as illustrated in FIG. 2, a hole-injection layer 211, a hole-transport layer 212, an electron-transport layer 216, and an electron-injection layer 217 are provided. As for structures of these layers, the structures of the respective layers described in Embodiment 2 may be applied. However, these layers are not necessarily provided and may be provided as appropriate depending on element characteristics.

Since the second light-emitting layer 215 in the light-emitting element described in this embodiment is formed using any of the bipolar oxadiazole derivatives described in Embodiment 1, the current efficiency of the light-emitting element can be increased.

Embodiment 4

Figure 3:
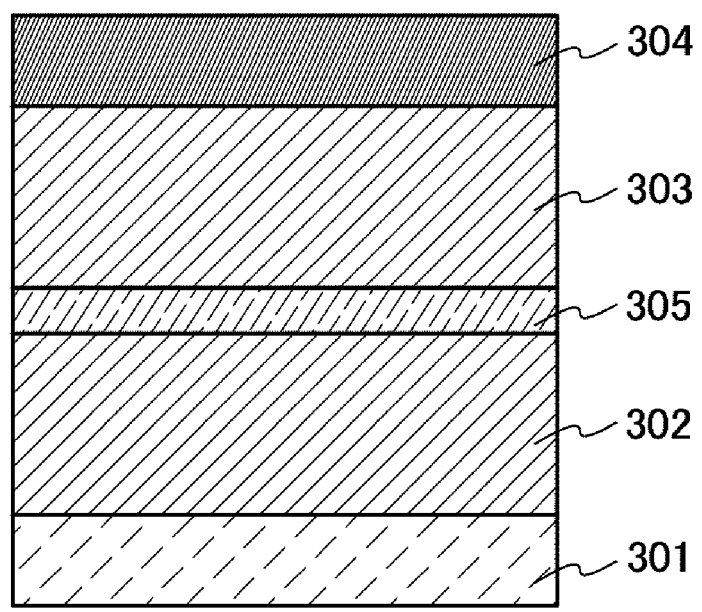
FIG. 3 illustrates a light-emitting element described in Embodiment 4.

In this embodiment, described is a light-emitting element including a plurality of EL layers, with reference to FIG. 3. The light-emitting element is a stacked-type element that has a plurality of EL layers (a first EL layer 302 and a second EL layer 303) between a first electrode 301 and a second electrode 304. Although the structure in which two EL layers are formed is described in this embodiment, a structure in which three or more EL layers are formed may be employed.

In this embodiment, the first electrode 301 functions as an anode, and the second electrode 304 functions as a cathode. Note that structures of the first electrode 301 and the second electrode 304 can be similar to those of the first electrode 101 and the second electrode 103 described in Embodiment 2. In addition, the plurality of EL layers (the first EL layer 302 and the second EL layer 303) each may have a structure similar to that of the EL layer 102 described in Embodiment 2, and any one of the EL layers may have a structure similar to that described in Embodiment 2. In other words, the structures of the first EL layer 302 and the second EL layer 303 may be the same or different from each other and can be similar to that of the EL layer 102 described in Embodiment 2.

Further, a charge-generation layer 305 is provided between the plurality of EL layers (the first EL layer 302 and the second EL layer 303). The charge-generation layer 305 has a function of injecting electrons into one of the EL layers and injecting holes into the other of the EL layers when voltage is applied between the first electrode 301 and the second electrode 304. In this embodiment, when voltage is applied such that the potential of the first electrode 301 is higher than that of the second electrode 304, the charge-generation layer 305 injects electrons into the first EL layer 302 and injects holes into the second EL layer 303.

Note that the charge-generation layer 305 preferably has a light-transmitting property in terms of light extraction efficiency. Further, the charge-generation layer 305 functions even when it has lower conductivity than the first electrode 301 or the second electrode 304.

The charge-generation layer 305 may have either a structure in which an electron acceptor is added to an organic compound having a high hole-transport property or a structure in which an electron donor is added to an organic compound having a high electron-transport property. Alternatively, both of these structures may be stacked.

In the case of the structure in which an electron acceptor is added to an organic compound having a high hole-transport property, the organic compound having a high hole-transport property can be, for example, an aromatic amine compound such as NPB, TPD, TDATA, MTDATA, or BSPB, or the like. Most of the substances mentioned here have a hole mobility of $10^{-6}$ cm$^2$/Vs or more.

Further, $F_4$-TCNQ, chloranil, and the like can be given as examples of the electron acceptor. In addition, a transition metal oxide can be given. Further, oxides of metals belonging to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Molybdenum oxide is especially preferable because of stability in air and a low hygroscopic property so as to be easily treated.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, instead of such a metal complex, PBD, OXD-7, TAZ, BPhen, BCP, or the like can be used. Most of the substances mentioned here have an electron mobility of $10^{-6}$ cm$^2$/Vs or more.

Further, as the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that formation of the charge-generation layer 305 by using the above materials can suppress an increase in driving voltage caused by the stack of the EL layers.

Although the light-emitting element having two EL layers has been described in this embodiment, the present invention can be similarly applied to a light-emitting element in which three or more EL layers are stacked. As in the case of the light-emitting element described in this embodiment, by arranging a plurality of EL layers to be partitioned from each other with a charge-generation layer between a pair of electrodes, light emission in a high luminance region can be achieved with current density kept low; thus, a light-emitting element having long lifetime can be realized. When the light-emitting element is applied for lighting, voltage drop due to resistance of an electrode material can be reduced, which can result in achieving homogeneous light emission in a large area. Moreover, a display device with low power consumption, which can be driven with a low voltage, can be obtained.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

A light-emitting element described in this embodiment has a plurality of EL layers. In addition, since at least one of the plurality of the EL layers has any of the light-emitting layers described in Embodiment 2 or 3, the current efficiency of the light-emitting element can be increased.

Embodiment 5

In this embodiment, described are a passive-matrix display device and an active-matrix display device which are manufactured using a light-emitting element.

FIGS. 4A to 4D and FIG. 5 illustrate examples of passive-matrix display devices.

In a passive-matrix (also referred to as simple-matrix) display device, a plurality of anodes arranged in stripes (in a stripe form) are provided to be perpendicular to a plurality of cathodes arranged in stripes. A light-emitting layer is interposed at each intersection, and therefore, by applying voltage to the light-emitting layer at an intersection of an anode selected and a cathode selected, the light-emitting layer emits light.

Figure 4A:
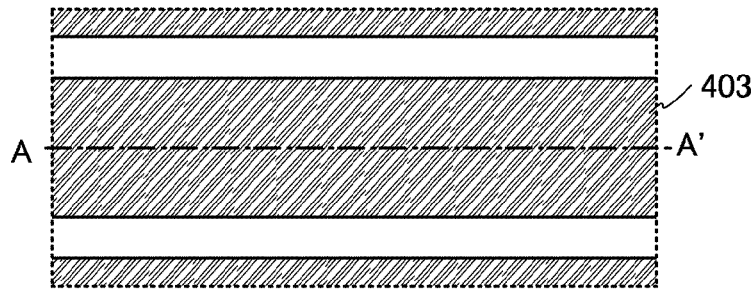
FIGS. 4A to 4D illustrate a passive-matrix display device described in Embodiment 5.
Figure 4B:
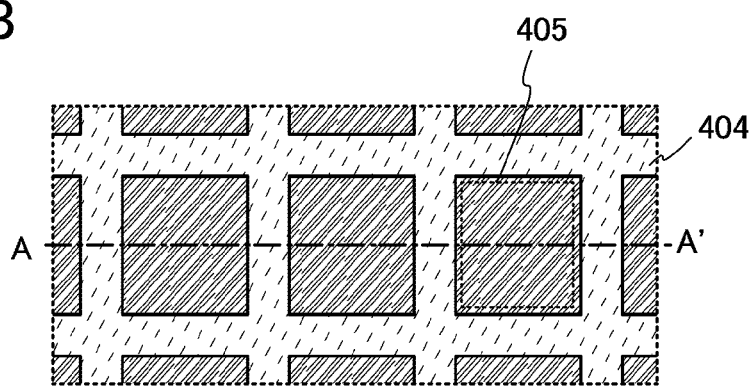
Figure 4C:
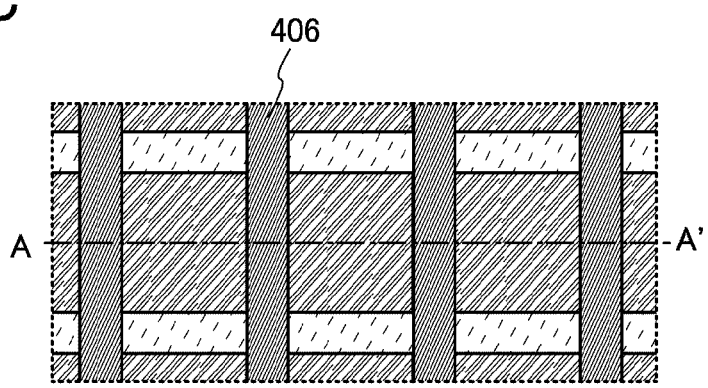
Figure 4D:
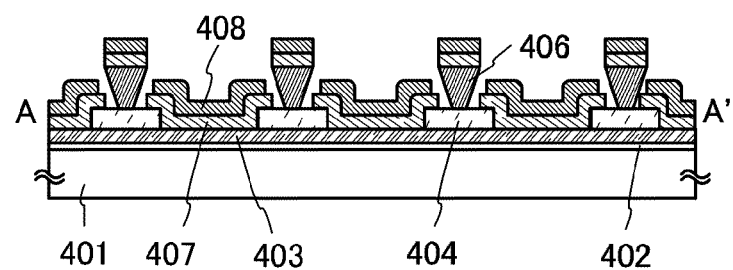

FIGS. 4A to 4C are top views illustrating a pixel portion before sealing. FIG. 4D is a cross-sectional view taken along chain line A-A' in FIGS. 4A to 4C.

An insulating layer 402 is formed as a base insulating layer over a substrate 401. Note that the base insulating layer may be omitted when unnecessary. A plurality of first electrodes 403 are arranged in stripes at regular intervals over the insulating layer 402 (see FIG. 4A).

In addition, a partition wall 404 having openings corresponding to each pixel is provided over the first electrodes 403. The partition wall 404 having openings is formed using an insulating material (a photosensitive or nonphotosensitive organic material (e.g., polyimide, acrylic, polyamide, polyimide amide, resist, or benzocyclobutene) or a spin on glass (SOG) film (e.g., a SiO$_x$ film containing an alkyl group). Note that openings 405 corresponding to each pixel serve as light-emitting regions (see FIG. 4B).

A plurality of inversely-tapered partition walls 406 parallel to each other are provided over the partition wall 404 having the openings to intersect with the first electrodes 403 (see FIG. 4C). The inversely-tapered partition walls 406 can be formed by a photolithography method. Here, light-exposure and development are performed on a negative-type photosensitive resin whose solubility to development decreases by light-exposure, resulting in the partition walls 406.

After the inversely-tapered partition walls 406 are formed as illustrated in FIG. 4C, EL layers 407 and second electrodes 408 are sequentially formed as illustrated in FIG. 4D. The total thickness of the partition wall 404 having the openings and the inversely-tapered partition wall 406 is set to be larger than the total thickness of the EL layer 407 and the second electrode 408; thus, as illustrated in FIG. 4D, EL layers 407 and second electrodes 408 which are separated for plural regions are formed. Note that the plurality of separated regions are electrically isolated from one another.

The second electrodes 408 are electrodes in stripes that are parallel to each other and extend along a direction intersecting with the first electrodes 403. Note that parts of a layer for forming the EL layers 407 and parts of a conductive layer for forming the second electrodes 408 are also formed over the inversely-tapered partition walls 406. These parts are separated from the EL layers 407 and the second electrodes 408.

Note that there is no particular limitation on the first electrode 403 and the second electrode 408 in this embodiment as long as one of them is an anode and the other is a cathode. Note that a stacked structure including the EL layer 407 may be adjusted as appropriate depending on the polarity of the electrode.

In addition, a sealing member such as a sealing can or a glass substrate may be attached to the substrate 401 with adhesive such as a sealant so that the light-emitting element can be placed in a sealed space, when necessary. In this manner, the light-emitting element can be prevented from deteriorating. The sealed space may be filled with filler or a dry inert gas. In addition, a desiccant or the like may be put between the substrate and the sealing member so that deterioration of the light-emitting element due to moisture or the like can be prevented. The desiccant removes a minute amount of moisture, thereby achieving sufficient desiccation. The desiccant can be a substance which absorbs moisture by chemical adsorption, such as an oxide of an alkaline earth metal typified by calcium oxide or barium oxide. Note that a substance which absorbs moisture by physical adsorption such as zeolite or silica gel may be used as well.

Figure 5:
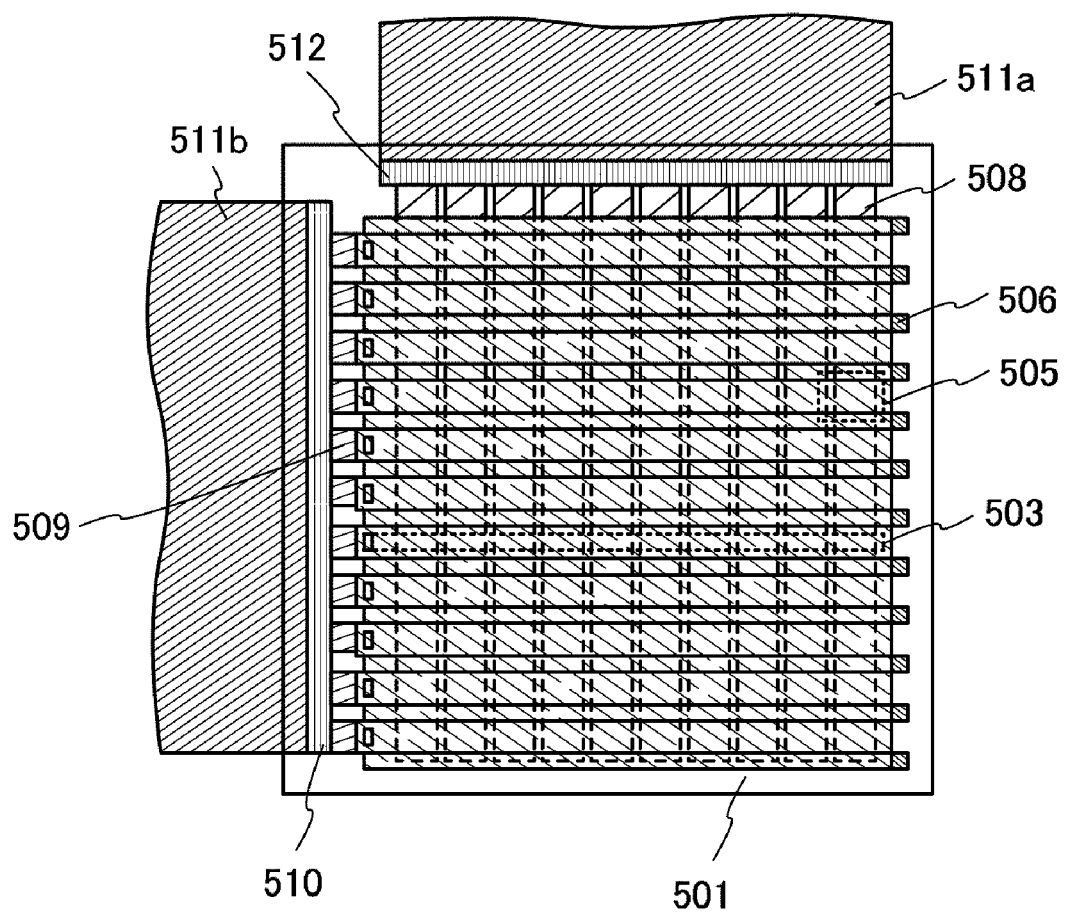
FIG. 5 illustrates a passive-matrix display device described in Embodiment 5.

FIG. 5 is a top view of the case where the passive-matrix display device illustrated in FIGS. 4A to 4D is provided with an FPC or the like.

As illustrated in FIG. 5, in a pixel portion forming an image display, scanning lines and data lines intersect with each other so that they are orthogonal to each other.

The first electrodes 403 in FIGS. 4A to 4D correspond to scanning lines 503 in FIG. 5; the second electrodes 408 in FIGS. 4A to 4D correspond to data lines 508 in FIG. 5; and the inversely-tapered partition walls 406 correspond to partition walls 506. The EL layers 407 illustrated in FIG. 4D are interposed between the data lines 508 and the scanning lines 503, and an intersection indicated by a region 505 corresponds to one pixel.

Note that the scanning lines 503 are electrically connected at their ends to connection terminals 509, and the connection terminals 509 are connected to an FPC 511*b* via an input terminal 510. The data lines 508 are connected to an FPC 511*a* via an input terminal 512.

When necessary, a polarizing plate, a circularly polarizing plate (including an elliptically polarizing plate), a retardation plate (a quarter-wave plate or a half-wave plate), or an optical film such as a color filter may be provided over a light-emitting surface as appropriate. Further, the polarizing plate or the circularly polarizing plate may be provided with an anti-reflection film. For example, anti-glare treatment may be carried out by which reflected light can be diffused by projections and depressions on the surface so as to reduce the reflection.

Although FIG. 5 illustrates the example in which a driver circuit is not provided over the substrate 501, an IC chip including a driver circuit may be mounted on the substrate 501.

When the IC chip is mounted, a data line side IC and a scanning line side IC, in each of which the driver circuit for transmitting a signal to a pixel portion is formed, are mounted on the periphery of (outside) the pixel portion by a COG method. The mounting may be performed using TCP or a wire bonding method instead of the COG method. TCP is a TAB tape mounted with an IC, and the TAB tape is connected to a wiring over an element formation substrate and the IC is mounted. Each of the data line side IC and the scanning line side IC may be formed using a silicon substrate or may be formed by formation of a driver circuit using a TFT over a glass substrate, a quartz substrate, or a plastic substrate.

Figure 6A:
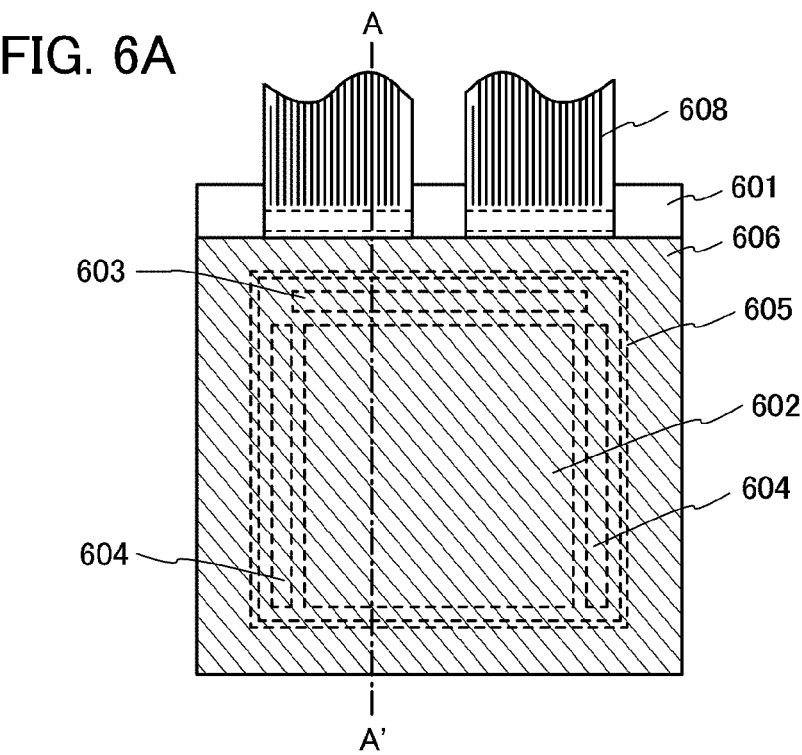
FIGS. 6A and 6B illustrate an active-matrix display device described in Embodiment 5.
Figure 6B:
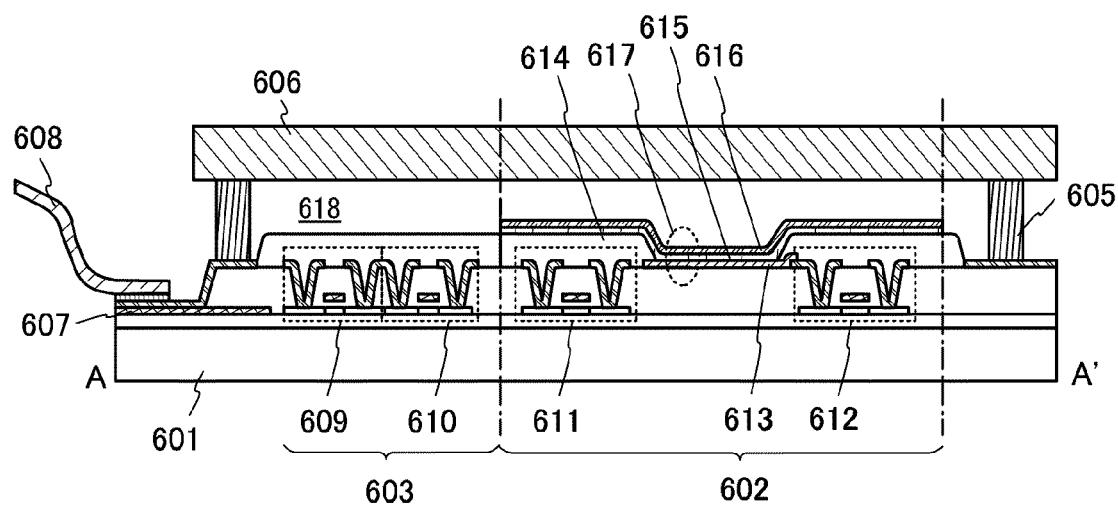

Next, an example of an active-matrix display device is described with reference to FIGS. 6A and 6B. Note that FIG. 6A is a top view illustrating a display device and FIG. 6B is a cross-sectional view taken along chain line A-A' in FIG. 6A. The active-matrix display device of this embodiment includes, over an element substrate 601, a pixel portion 602, a driver circuit portion (a source side driver circuit) 603, and driver circuit portions (a gate side driver circuits) 604. The pixel portion 602, the driver circuit portion 603, and the driver circuit portions 604 are sealed with a sealant 605 between the element substrate 601 and a sealing substrate 606.

In addition, over the element substrate 601, a lead wiring 607 for connecting an external input terminal, through which a signal (e.g., a video signal, a clock signal, a start signal, a reset signal, or the like) or electric potential from the outside is transmitted to the driver circuit portion 603 and the driver circuit portion 604, is provided. Here, an example is described in which a flexible printed circuit (FPC) 608 is provided as the external input terminal. Although only the FPC 608 is illustrated here, the FPC 608 may have a printed wiring board (PWB) attached. The display device in this specification includes not only a display device itself but also a state in which an FPC or a PWB is attached thereto.

Next, a cross-sectional structure will be described with reference to FIG. 6B. The driver circuit portions and the pixel portion are formed over the element substrate 601; here in FIG. 6B, the pixel portion 602 and the driver circuit portion 603 which is the source side driver circuit are illustrated.

An example is illustrated in which a CMOS circuit which is a combination of an n-channel TFT 609 and a p-channel TFT 610 is formed as the driver circuit portion 603. Note that a circuit included in the driver circuit portion may be formed using various CMOS circuits, PMOS circuits, or NMOS circuits. Although a driver circuit-integrated type in which the driver circuit is formed over the substrate is described in this embodiment, the driver circuit is not necessarily formed over the substrate, and the driver circuit can be formed outside, not over the substrate.

Further, the pixel portion 602 has a plurality of pixels, each including a switching TFT 611, a current control TFT 612, and an anode 613 electrically connected to a wiring (a source electrode or a drain electrode) of the current control TFT 612. An insulator 614 is formed so as to cover an edge portion of the anode 613. In this embodiment, the insulator 614 is formed using a positive photosensitive acrylic resin.

In addition, in order to obtain favorable coverage by a film which is to be stacked over the insulator 614, the insulator 614 is preferably formed so as to have a curved surface with curvature at an upper edge portion or a lower edge portion. For example, in the case of using a positive photosensitive acrylic resin as a material for the insulator 614, the insulator 614 is preferably formed so as to have a curved surface with a curvature radius (0.2 μm to 3 μm) at the upper edge portion. Either a negative photosensitive material which becomes insoluble in an etchant by light of a specific wavelength or a positive photosensitive material which becomes soluble in an etchant by light of a specific wavelength can be used for the insulator 614. Without limitation to an organic compound, an inorganic compound such as silicon oxide or silicon oxynitride can be used for the insulator 614.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as a wiring of the current control TFT 612 which is connected to the anode 613, resistance of the wiring can be low and favorable ohmic contact with the ITO film can be obtained. Note that, although not illustrated, the cathode 616 is electrically connected to the FPC 608 which is an external input terminal.

Note that in the EL layer 615, at least a light-emitting layer is provided, and in addition to the light-emitting layer, a hole-injection layer, a hole-transport layer, an electron-transport layer, and an electron-injection layer are provided as appropriate. A light-emitting element 617 is formed of a stacked structure of the anode 613, the EL layer 615, and the cathode 616.

In addition, although the cross-sectional view of FIG. 6B illustrates only one light-emitting element 617, a plurality of light-emitting elements are arranged in a matrix form in the pixel portion 602. Light-emitting elements that emit light of three kinds of colors (R, G, and B) are formed in the pixel portion 602, whereby a display device capable of full color display can be obtained. Alternatively, a display device which is capable of full color display may be manufactured by a combination with color filters.

By attachment of the sealing substrate 606 to the element substrate 601 with the sealant 605, a structure in which the light-emitting element 617 is provided in a space 618 surrounded by the element substrate 601, the sealing substrate 606, and the sealant 605 is obtained. Note that the space 618 may be filled with an inert gas (such as nitrogen and argon) or the sealant 605.

It is preferable to use an epoxy-based resin for the sealant 605. In addition, preferably, the material does not transmit moisture or oxygen as much as possible. As the sealing substrate 606, a plastic substrate formed of FRP (fiberglass-reinforced plastics), PVF (polyvinyl fluoride), polyester, acrylic, or the like can be used instead of a glass substrate or a quartz substrate.

In the above manner, an active-matrix display device can be obtained.

Since the display device of this embodiment is manufactured using any of the light-emitting elements having high current efficiency described in Embodiments 2 to 4, the power consumption of the display device can be reduced.

Embodiment 6

Figure 7A:
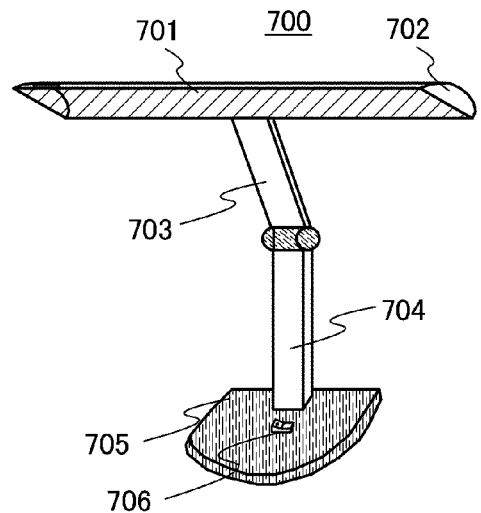
FIGS. 7A to 7C illustrate lighting devices described in Embodiment 6.
Figure 7B:
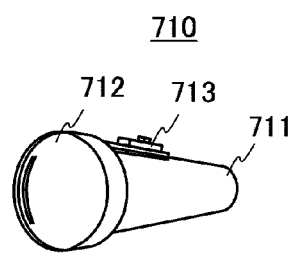
Figure 7C:
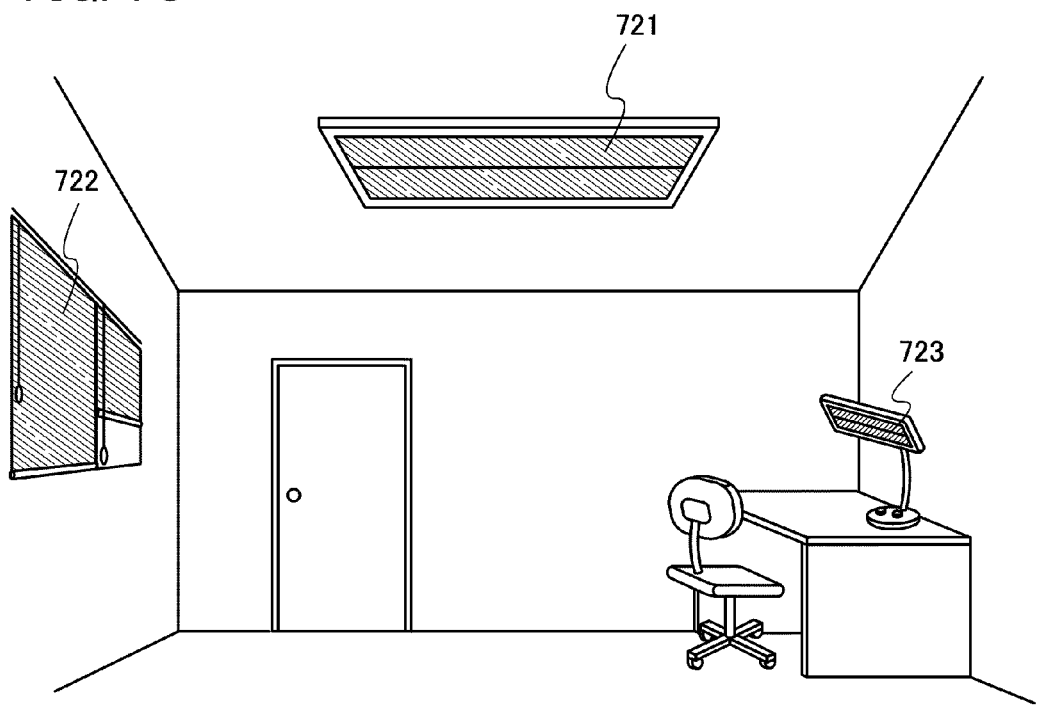

In this embodiment, described are lighting devices which are manufactured using a light-emitting element, with reference to FIGS. 7A to 7C.

Examples of lighting devices include the following: indoor lighting device which is used by being provided indoors, such as downlight, pendant light, ceiling light, and bracket light; indoor lighting device which can be moved, such as a stand light on a desk or table; lighting device which is mainly used outside, such as headlamp, penlight, and hand lamp; and the like.

FIG. 7A illustrates an example of a stand light. A stand light 700 includes an illuminating portion 701, a shade 702, an adjustable arm 703, a support 704, a base 705, and a power supply switch 706. Note that in the illuminating portion 701, any of the light-emitting elements described in Embodiments 2 to 4 is used.

FIG. 7B illustrates an example of a hand lamp. A hand lamp 710 includes a housing 711, an illuminating portion 712, and a power supply switch 713. Note that in the illuminating portion 712, any of the light-emitting elements described in Embodiments 2 to 4 is used.

FIG. 7C illustrates an example of indoor lighting devices. The light-emitting device can be formed to have a large area and therefore can be used as a ceiling light 721. Alternatively, the light-emitting device can be used as a roll-type lighting device 722. Note that as illustrated in FIG. 7C, a stand light 723 (the stand light 700) described with reference to FIG. 7A may be used together in a room provided with the indoor lighting devices.

The lighting devices of this embodiment are manufactured using any of the light-emitting elements having high current efficiency described in Embodiments 2 to 4. The power consumption of the lighting devices can be reduced accordingly.

Embodiment 7

In this embodiment, described are examples of electronic devices which are manufactured using a light-emitting element, with reference to FIGS. 8A to 8D.

Examples of the electronic devices to which the light-emitting element is applied include television sets (also referred to as televisions or television receivers), monitors of computers or the like, cameras such as digital cameras or digital video cameras, digital photo frames, cellular phones (also referred to as cellular phone sets), portable game consoles, portable information terminals, audio reproducing devices, large-sized game machines such as pachinko machines, and the like. Some specific examples of these electronic devices are illustrated in FIGS. 8A to 8D.

Figure 8A:
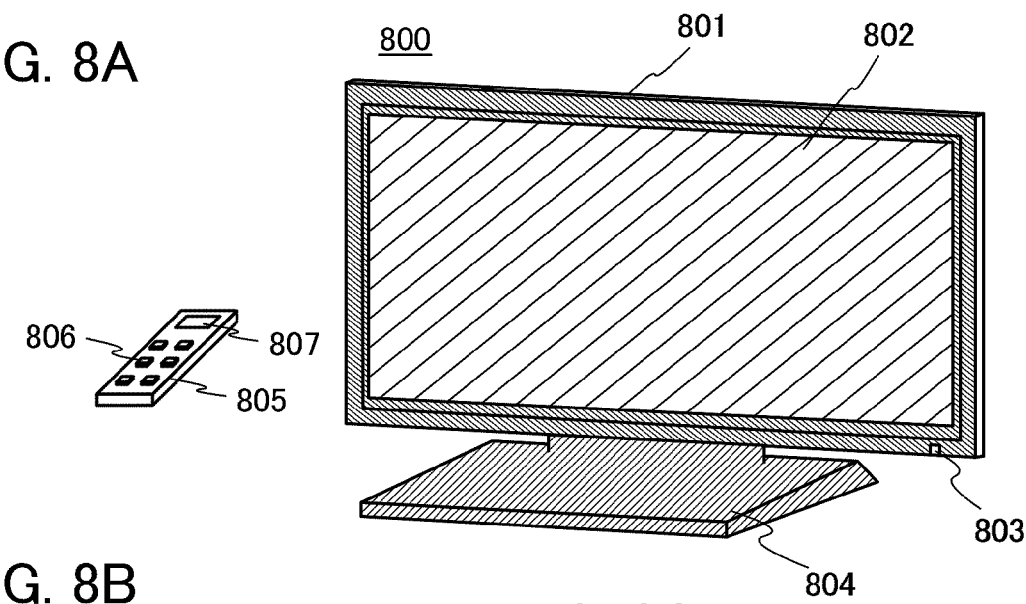
FIGS. 8A to 8D illustrate electronic devices described in Embodiment 7.

FIG. 8A illustrates an example of a television set. In a television set 800, a display portion 802 is incorporated in a central portion of a housing 801, and an illuminating portion 803 is incorporated in a corner thereof. The display portion 802 can display images, and the illuminating portion 803 can illuminate when an image is displayed by the display portion 802. Note that the television set 800 uses any of the light-emitting elements described in Embodiments 2 to 4 in either the display portion 802 or the illuminating portion 803, or both the display portion 802 and the illuminating portion 803. Here, the housing 801 is supported by a stand 804.

The television set 800 can be operated with an operation switch of the housing 801 or a separate remote controller 805. Channels and volume can be controlled with an operation key 806 of the remote controller 805 so that an image displayed on the display portion 802 can be controlled. Furthermore, the remote controller 805 may be provided with a display portion 807 for displaying data output from the remote controller 805.

Note that the television set 800 is provided with a receiver, a modem, and the like. With the use of the receiver, general television broadcasting can be received. Moreover, when the television set is connected to a communication network with or without wires via the modem, one-way (from a sender to a receiver) or two-way (between a sender and a receiver or between receivers) information communication can be performed.

Figure 8B:
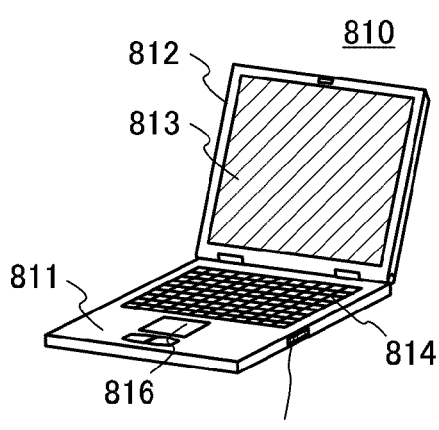

FIG. 8B illustrates an example of a computer. A computer 810 includes a main body 811, a housing 812, a display portion 813, a keyboard 814, an external connecting port 815, a pointing device 816, and the like. Note that the computer 810 is manufactured by using any of the light-emitting elements described in Embodiments 2 to 4 for the display portion 813.

Figure 8C:
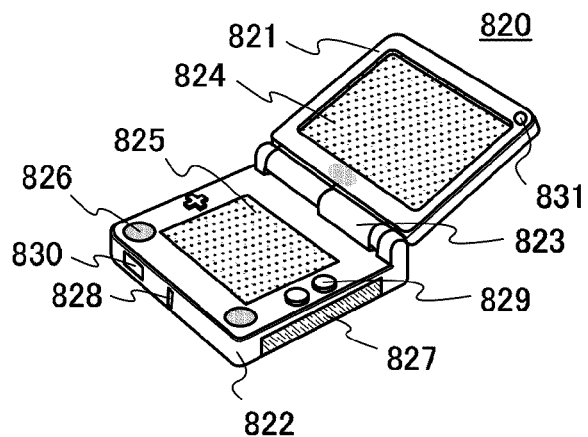

FIG. 8C illustrates an example of a portable amusement machine. A portable amusement machine 820 includes two housings: a housing 821 and a housing 822. The housings 821 and 822 are connected with a connection portion 823 so that the portable amusement machine can be opened and closed. A display portion 824 is incorporated in the housing 821, and a display portion 825 and an illuminating portion 828 are incorporated in the housing 822. In addition, the portable amusement machine 820 illustrated in FIG. 8C includes a speaker portion 826, a recording medium insertion portion 827, an input means (an operation key 829, a connection terminal 830, a sensor 831 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays)), and the like. It is needless to say that the structure of the portable amusement machine is not limited to the above as long as any of the light-emitting elements described in Embodiments 2 to 4 is used for at least one of the display portion 824, the display portion 825, and the illuminating portion 828. The portable amusement machine may include other accessory equipment as appropriate. The portable amusement machine 820 illustrated in FIG. 8C has a function of reading a program or data stored in a recording medium to display it on the display portion, and a function of sharing information with another portable amusement machine by wireless communication. The portable amusement machine 820 illustrated in FIG. 8C can have any other various functions without limitation to the above.

Figure 8D:
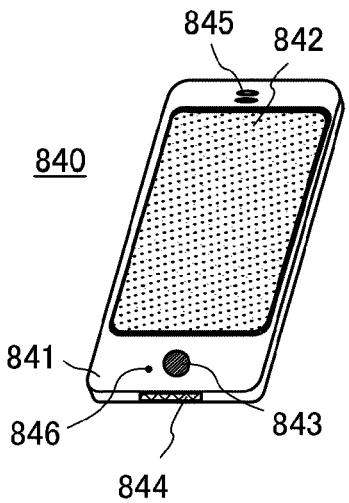

FIG. 8D illustrates an example of a cellular phone. A cellular phone 840 is provided with a display portion 842 incorporated in a housing 841, an operation button 843, an external connection port 844, a speaker 845, a microphone 846, and the like. Note that any of the light-emitting elements described in Embodiments 2 to 4 is used for the display portion 842 of the cellular phone 840.

When the display portion 842 of the cellular phone 840 illustrated in FIG. 8D is touched with a finger or the like, data can be input. Furthermore, operations such as making a call and texting a massage can be performed by touching the display portion 842 with a finger or the like.

There are mainly three screen modes for the display portion 842. The first mode is a display mode mainly for displaying images. The second mode is an input mode mainly for inputting data such as text. The third mode is a display-and-input mode in which two modes of the display mode and the input mode are combined.

For example, in order to make a call or text a message, the display portion 842 is set to a text input mode mainly for inputting text, and text can be input on a screen. In this case, a keyboard or number buttons are preferably displayed on the display portion 842.

By providing a detection device which includes a sensor for detecting inclination, such as a gyroscope or an acceleration sensor, inside the cellular phone 840, the direction of the cellular phone 840 (whether it stands upright or is laid down on its side for a landscape mode or a portrait mode) is determined so that display on the screen of the display portion 842 can be automatically switched.

In addition, the screen mode is switched by, for example, touching the display portion 842 or operating the operation button 843 of the housing 841. Alternatively, the screen mode may be switched depending on the kind of images displayed on the display portion 842. For example, when a signal of an image displayed on the display portion 842 is of moving image data, the screen mode is switched to the display mode. When the signal is of text data, the screen mode is switched to the input mode.

Moreover, in the input mode, when input by touching the display portion 842 is not performed within a specified period while a signal detected by the optical sensor in the display portion 842 is detected, the screen mode may be controlled so as to be switched from the input mode to the display mode.

The display portion 842 may function as an image sensor. For example, an image of a palm print, a fingerprint, or the like is taken by touching the display portion 842 with the palm or the finger, whereby personal authentication can be performed. Furthermore, by providing a backlight or a sensing light source emitting a near-infrared light for the display portion, an image of a finger vein, a palm vein, or the like can also be taken.

Since the lighting devices and the electronic devices of this embodiment are provided with any of the light-emitting elements described in Embodiments 2 to 4, the power consumption can be reduced.

Example 1

In this example, described is a method for synthesizing the oxadiazole derivative represented by Structural Formula (100) below, 9-phenyl-3-[4-(5-phenyl-1,3,4-oxadiazol-2-yl)phenyl]-9H-carbazole (abbreviation: PCO11).

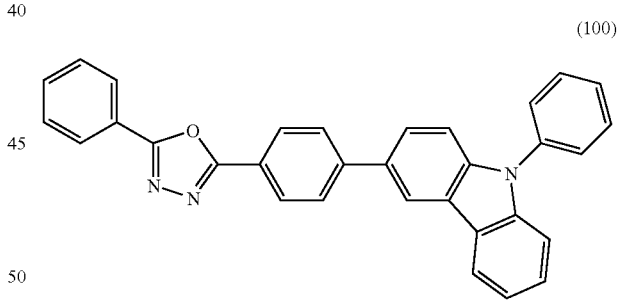

(100)

Into a 50 mL three-neck flask were put 3.0 g (10 mmol) of 2-(4-bromophenyl)-5-phenyl-1,3,4-oxadiazole (Compound a1), 3.4 g (12 mmol) of 9-phenyl-9H-carbazol-3-boronic acid (Compound b1), 0.010 g (0.045 mmol) of palladium(II) acetate, and 0.030 g (0.99 mmol) of tri(o-tolyl)phosphine. Into the 50 mL flask were further added 30 mL of a 2M aqueous solution of potassium carbonate and 60 mL of toluene. Next, the mixture was degassed under low pressure, the atmosphere in the 50 mL three-neck flask was substituted by nitrogen, and the mixture was stirred at 100° C. for 5 hours under a nitrogen stream. After stirring, toluene was added to the mixture, and a suspension was obtained. After this suspension was washed with water, magnesium sulfate was added to an organic layer to dry the organic layer. Further, suction filtration was performed through Celite (produced by Wako Pure Chemical Industries, Ltd., Catalog No. 531-16855), and a filtrate was obtained. A compound obtained by concentrating the filtrate was purified by silica gel column chromatography. The column chromatography was performed first using toluene as a developing solvent and then using a mixed solvent of toluene:ethyl acetate=9:1 as a developing solvent. The compound obtained by concentrating the obtained fractions was recrystallized with a mixed solvent of chloroform and hexane. As a result, 2.2 g of a powdery white solid was obtained in a yield of 48%. Synthesis Scheme (a-1) of this example is represented below.

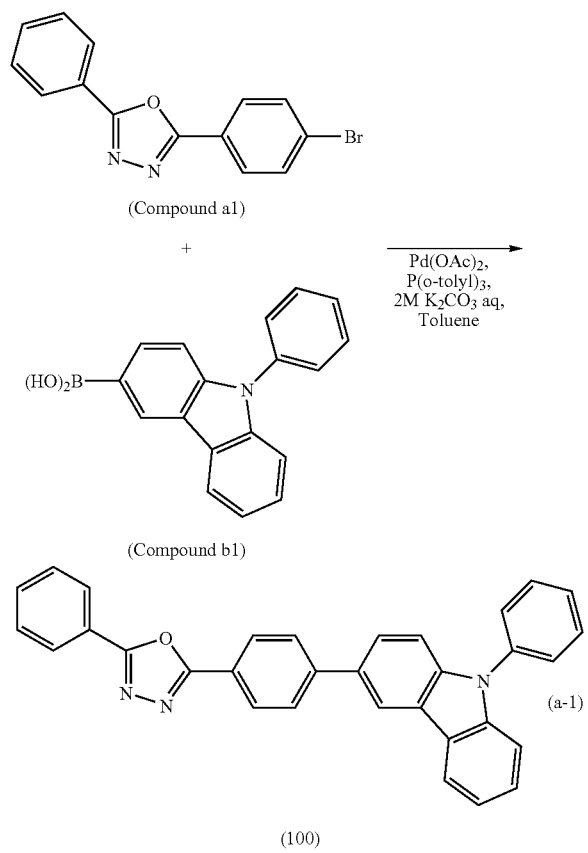

Sublimation purification of 2.2 g of the obtained solid was performed by a train sublimation method. The sublimation purification was conducted under a low pressure of 7.0 Pa, an argon flow rate of 3.0 mL/min, at 260° C. for 17 hours. The yield was 1.4 g (64%).

The compound obtained by the above method was measured by a nuclear magnetic resonance (NMR) method. The measurement data are as follows: $^1$H-NMR (CDCl$_3$, 300 MHz): δ=7.29-7.73 (m, 13H), 7.89 (d, J=8.8 Hz, 2H), 8.16-8.26 (m, 5H), 8.42 (s, 1H).

Figure 9A:
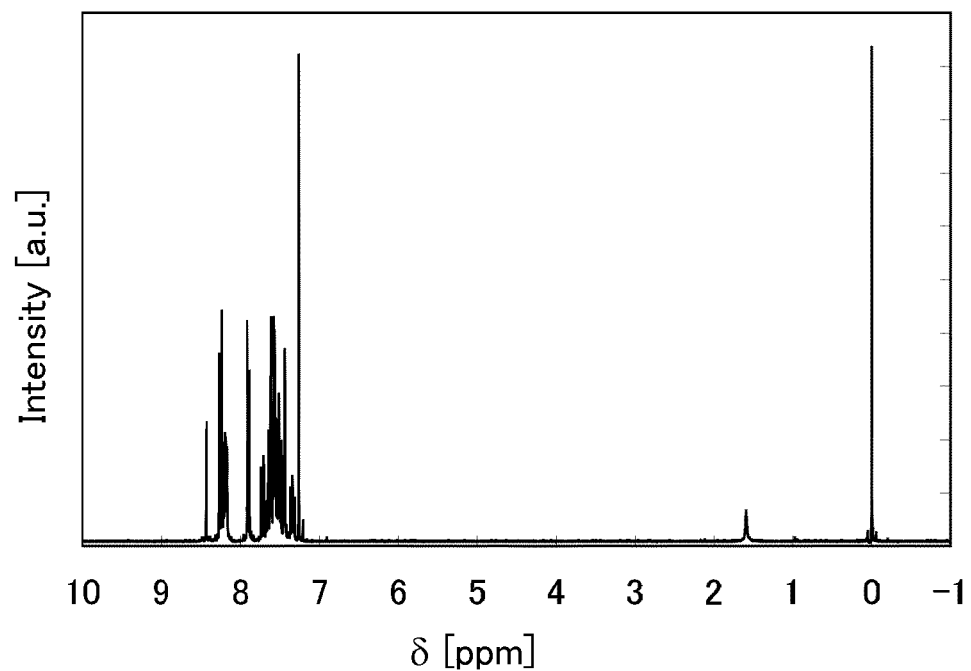
FIGS. 9A and 9B each show a $^1$H-NMR chart of PCO11 (abbreviation) represented by Structural Formula (100)
Figure 9B:
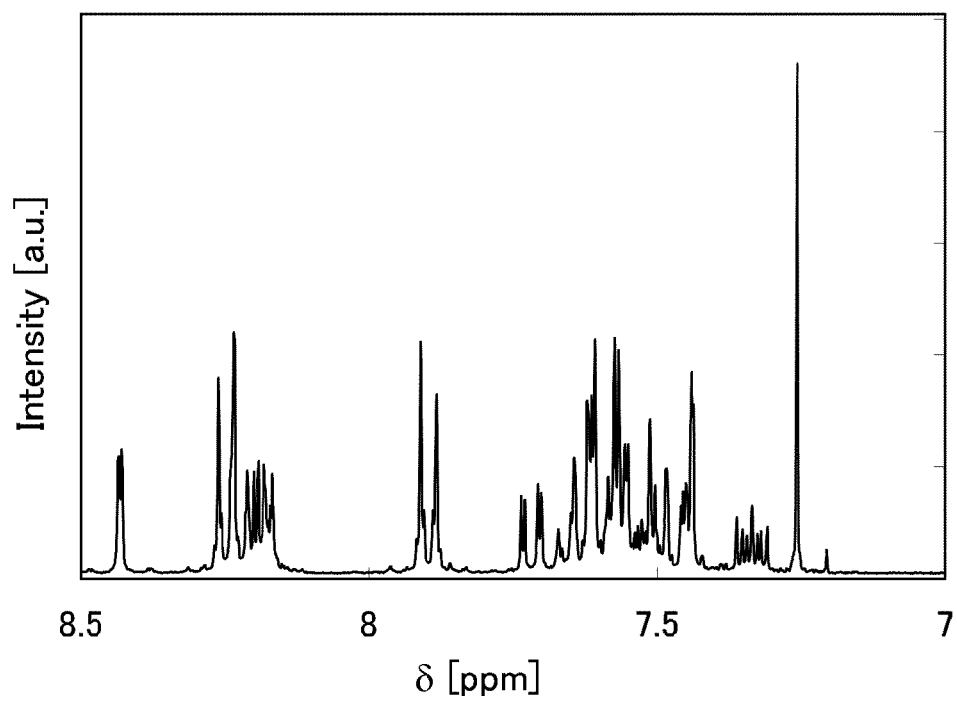

The $^1$H-NMR chart of the compound obtained by the above method is shown in FIGS. 9A and 9B. Note that FIG. 9B is a chart showing an enlarged view of the range of 7.0 ppm to 8.5 ppm in FIG. 9A. The measurement result indicates that 9-phenyl-3-[4-(5-phenyl-1,3,4-oxadiazol-2-yl)phenyl]-9H-carbazole (abbreviation: PCO11), which is the oxadiazole derivative represented by Structural Formula (100) above was obtained.

Figure 10A:
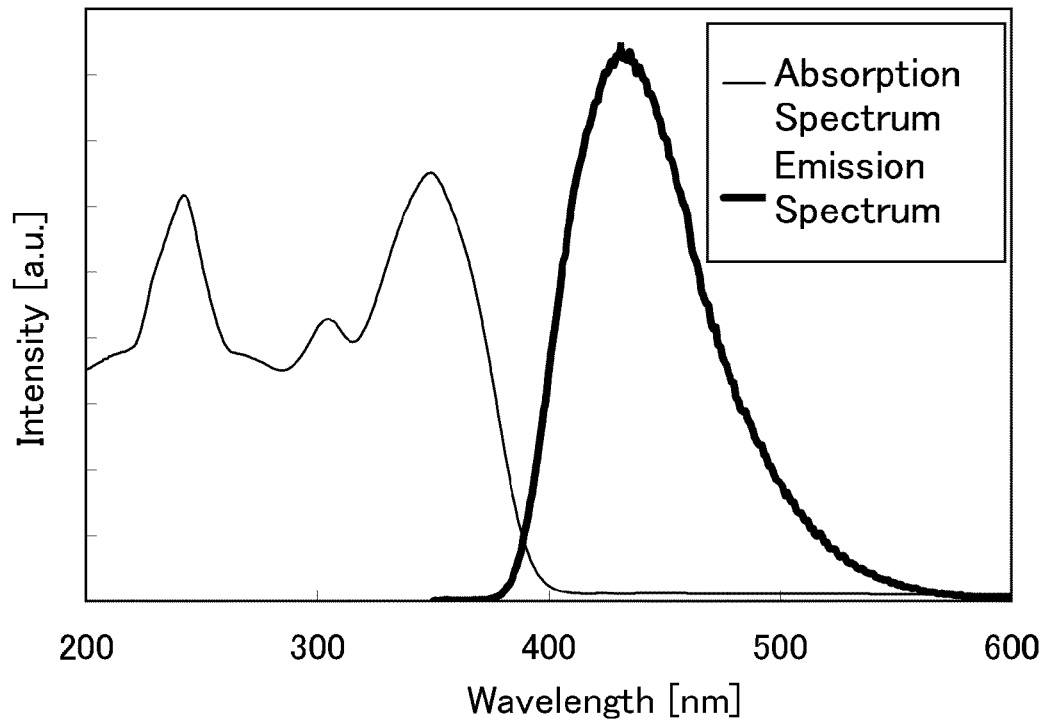
FIG. 10A shows an ultraviolet-visible absorption spectrum and an emission spectrum of a solution sample of PCO11 (abbreviation) represented by Structural Formula (100)
Figure 10B:
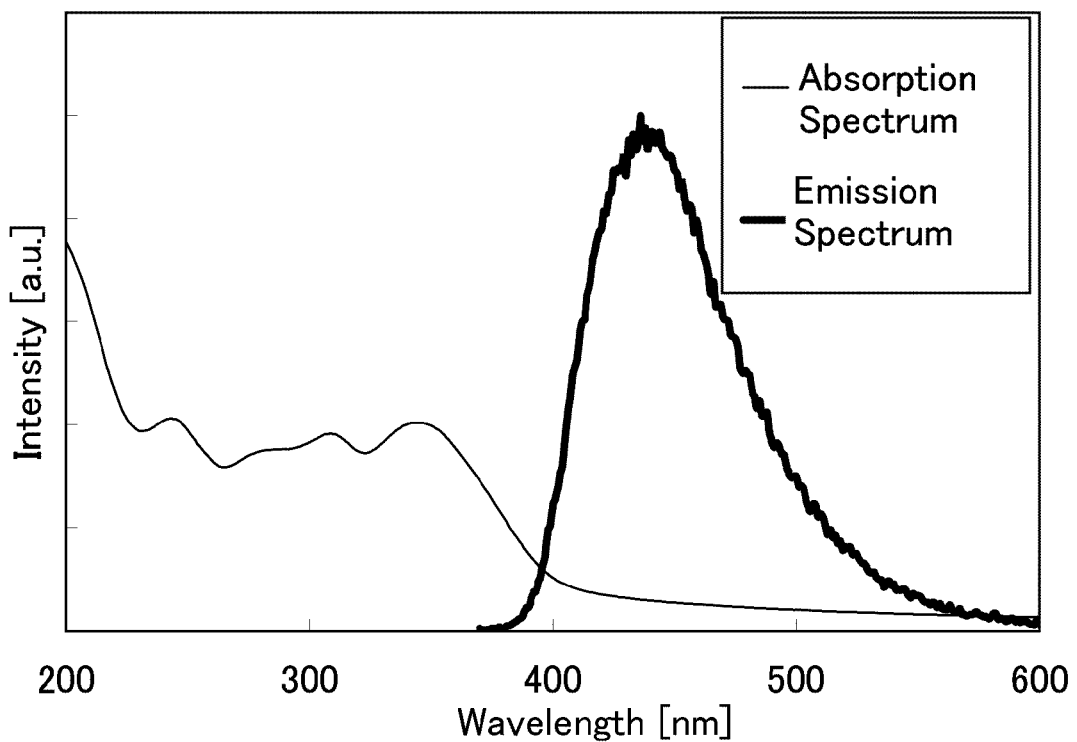
FIG. 10B shows an ultraviolet-visible absorption spectrum and an emission spectrum of a thin-film sample thereof.

FIGS. 10A and 10B show absorption spectra and emission spectra of PCO11 measured by using an ultraviolet-visible spectrophotometer. Note that the absorption spectra and the emission spectra of PCO11 were measured using a sample of a dichloromethane solution of PCO11 in a quartz cell and a sample of a thin film of PCO11 which had been evaporated on a quartz substrate. Specifically, FIG. 10A shows spectra obtained using the solution sample, and FIG. 10B shows spectra obtained using the thin-film sample. In addition, for the purpose of evaluating only the absorption spectra from PCO11, in the case of the solution sample, the absorption spectrum of FIG. 10A is obtained by subtracting the absorption spectra of quartz and dichloromethane from the actually obtained absorption spectrum. As for the thin-film sample, the absorption spectrum of FIG. 10B is obtained by subtracting the absorption spectrum of quartz from the actually obtained absorption spectrum.

In FIGS. 10A and 10B, the horizontal axes indicate wavelength (nm) and the vertical axes indicate intensity (arbitrary unit). In the case of the dichloromethane solution sample, the absorption peak is observed at 329 nm, and the maximum emission wavelength is observed at 436 nm (excitation wavelength: 340 nm) (see FIG. 10A). In the case of the thin-film sample, the absorption peak is observed at 344 nm, and the maximum emission wavelength is observed at 436 nm (excitation wavelength: 344 nm) (see FIG. 10B).

A measurement result of the HOMO level and the LUMO level of the thin-film sample of PCO11 is shown. Specifically, first, the value of the ionization potential which had been measured with a photoelectron spectrometer (AC-2, produced by Riken Keiki Co., Ltd.) in air was converted into a negative value, and then the HOMO level was obtained. Next, the absorption edge was obtained from Tauc plot, with an assumption of direct transition, using data on the absorption spectrum in FIG. 10B, it was added as an optical energy gap to the value of the HOMO level, and then the LUMO level was obtained. As a result, the HOMO level of PCO11 was −5.53 eV, and the LUMO level thereof was −2.23 eV (the optical energy gap was 3.20 eV). PCO11 therefore was revealed to have a large energy gap.

Figure 11A:
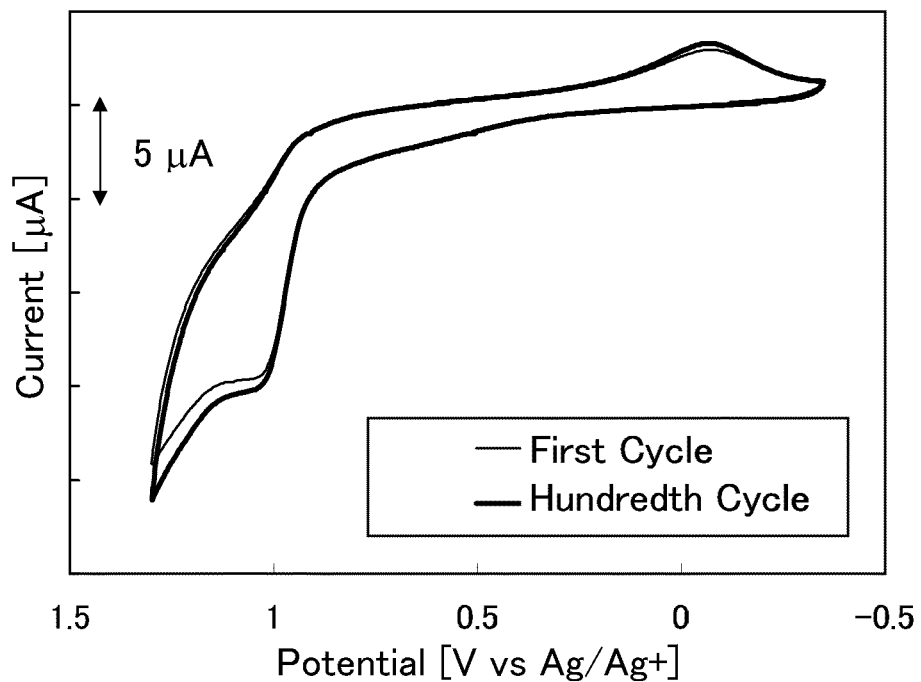
FIGS. 11A and 11B show oxidation characteristics and reduction characteristics, respectively, of PCO11 (abbreviation) represented by Structural Formula (100)
Figure 11B:
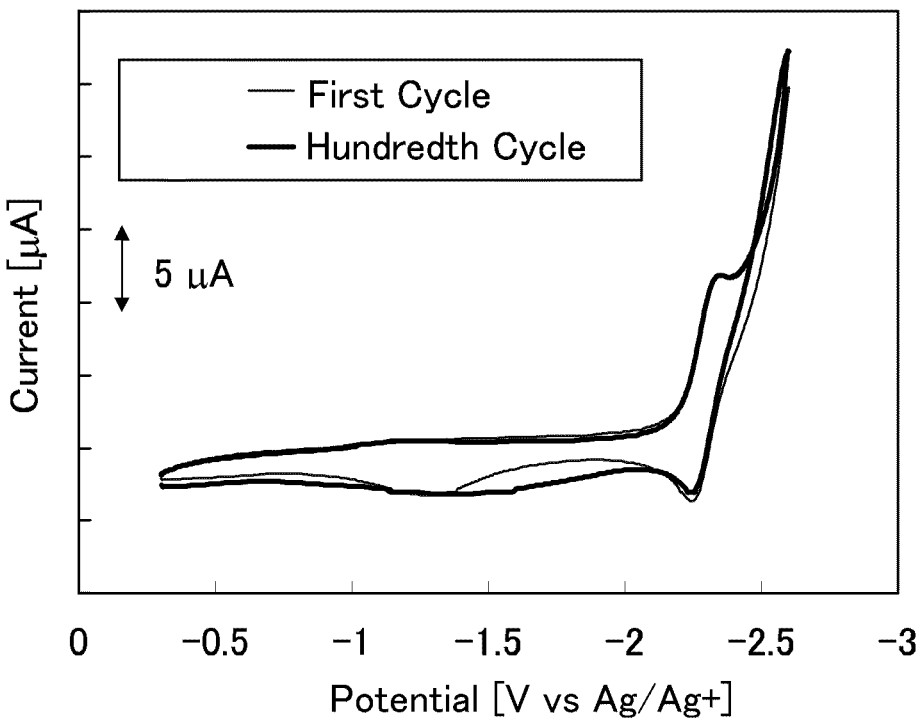

FIGS. 11A and 11B show measurement results of oxidation-reduction characteristics of PCO11. Note that FIG. 11A shows oxidation characteristics, and FIG. 11B shows reduction characteristics. The oxidation-reduction reaction characteristics were measured by cyclic voltammetry (CV). Note that an electrochemical analyzer (ALS model 600A, produced by BAS Inc.) was used for the measurement.

For a solution used in the CV measurements, dehydrated dimethylformamide (DMF, produced by Sigma-Aldrich Inc., 99.8%, Catalog No. 22705-6) was used as a solvent. Tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, the concentration of PCO11, which was to be measured, was adjusted to 1 mmol/L. In addition, a platinum electrode (PTE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE5 reference electrode for nonaqueous solvent, produced by BAS Inc.) was used as a reference electrode. Note that the measurements were conducted at room temperature.

The oxidation characteristics of PCO11 were examined as follows. A scan for changing the potential of the working electrode with respect to the reference electrode from −0.35 V to 1.30 V and then from 1.30 V to −0.35 V was set to one cycle, and the measurement was performed for 100 cycles. Note that the scanning speed of the CV measurement was set to be 0.1 V/s. In addition, FIG. 11A shows only the CV charts at the first cycle and the hundredth cycle.

The reduction characteristics of PCO11 were examined as follows. A scan for changing the potential of the working electrode with respect to the reference electrode from −0.30 V to −2.60 V and then from −2.60 V to −0.30 V was set to one cycle, and the measurement was performed for 100 cycles. Note that the scanning speed of the CV measurement was set to be 0.1 V/s. In addition, FIG. 11B shows only the CV charts at the first cycle and the hundredth cycle.

In each of FIGS. 11A and 11B, the horizontal axis shows potential (V) of the working electrode with respect to the reference electrode, while the vertical axis shows a value (μA) of current flowing between the working electrode and the auxiliary electrode. FIG. 11A reveals that PCO11 has a peak indicating oxidation at +0.99 V (vs. Ag/Ag$^+$ electrode). In addition, FIG. 11B reveals that PCO11 has a peak indicating reduction at −2.30 V (vs. Ag/Ag$^+$ electrode).

FIGS. 11A and 11B show no significant change in the position and intensity of the peaks in CV curves of the oxidation and reduction between the first cycle and the hundredth cycle, thereby indicating that PCO11 is stable to repetitive oxidation and reduction.

In addition, the optimal molecular structure of PCO11 in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable high speed and highly accurate calculations. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of is to 4s and 2p to 4p are considered in the case of carbon atoms. Furthermore, to improve calculation accuracy, the p function and the d function as polarization basis sets were added respectively to hydrogen atoms and atoms other than hydrogen atoms.

Note that Gaussian 03 was used as a quantum chemistry computational program. A high performance computer (produced by SGI Japan, Ltd., Altix 4700) was used for the calculations.

Figure 12A:
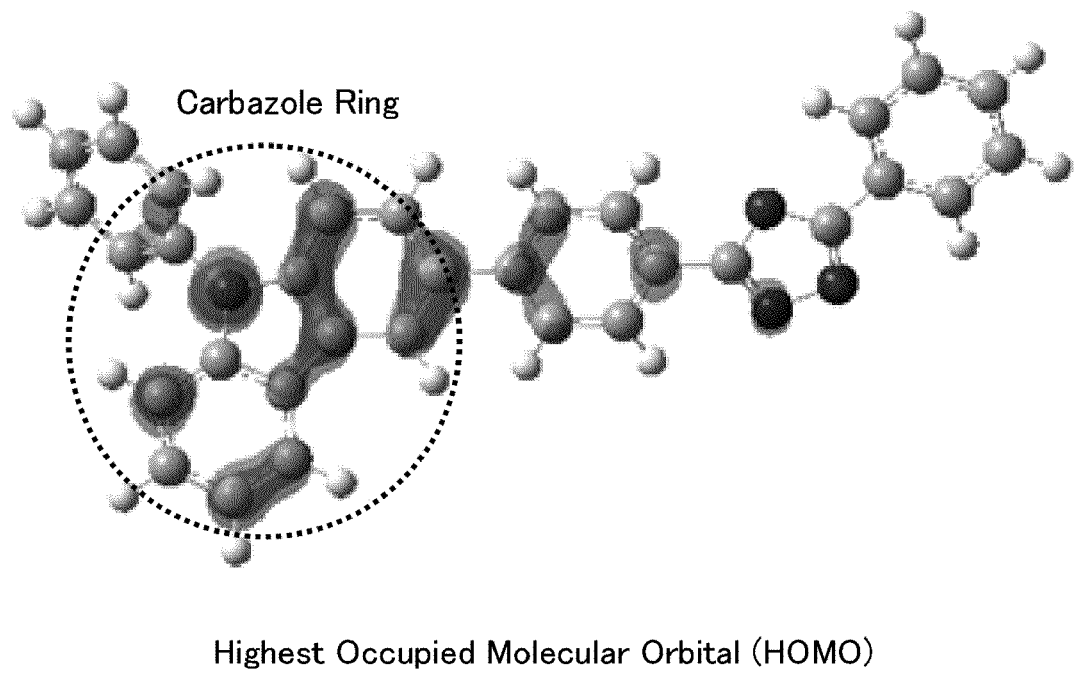
FIGS. 12A and 12B show a highest occupied molecular orbital (HOMO) and a lowest unoccupied molecular orbital (LUMO), respectively, of PCO11 (abbreviation) which are obtained by simulation.
Figure 12B:
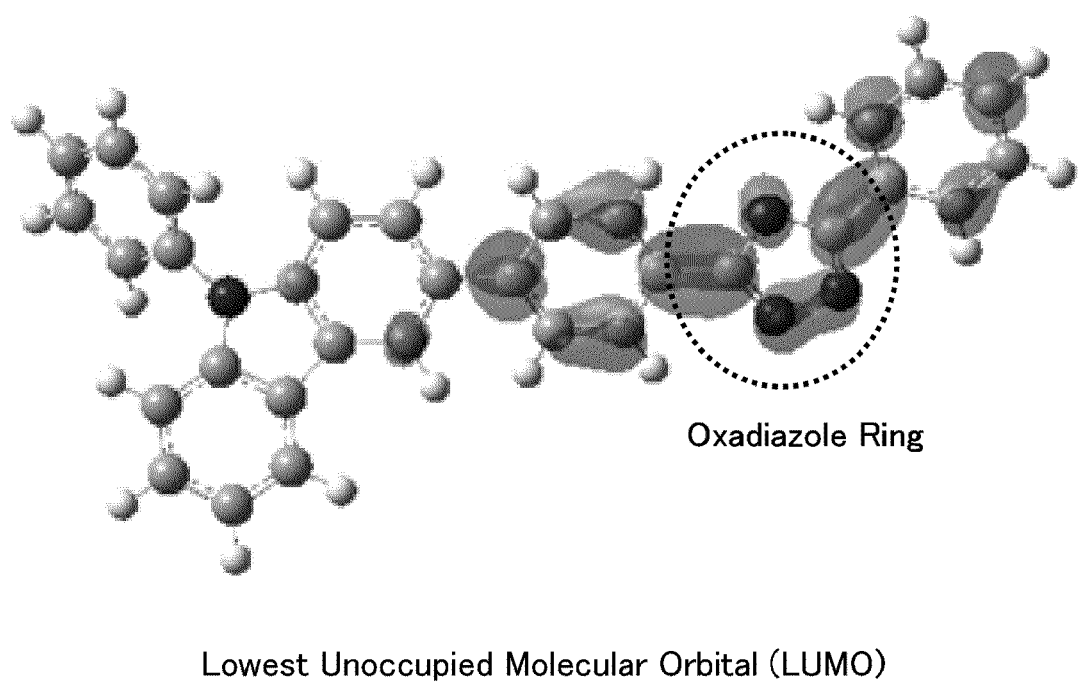

FIGS. 12A and 12B show respectively the highest occupied molecular orbital (HOMO) and lowest unoccupied molecular orbital (LUMO) of PCO11, which were found by the calculations. FIG. 12A shows the HOMO, and FIG. 12B shows the LUMO. In the drawings, the spheres represent atoms forming PCO11 and cloud-like objects around atoms represent orbits. Note that FIGS. 12A and 12B are visualization views of calculation results of the optimal molecular structures obtained by Gaussview 4.1, which is software visualizing computational results.

FIGS. 12A and 12B reveal that a HOMO and a LUMO of PCO11 exist in a carbazole ring and an oxadiazole ring, respectively. In other words, the carbazole ring contributes to the hole-transport property of PCO11 while the oxadiazole ring contributes to the electron-transport property thereof. The carbazole ring is a unit exhibiting a high hole-transport property, and the oxadiazole ring is a unit exhibiting a high electron-transport property. From the above, it is found that PCO11 is bipolar.

Example 2

In this example, described is a method for synthesizing the oxadiazole derivative represented by Structural Formula (121) below, 3,9-diphenyl-6-[4-(5-phenyl-1,3,4-oxadiazol-2-yl)phenyl]-9H-carbazole (abbreviation: PCO11II).

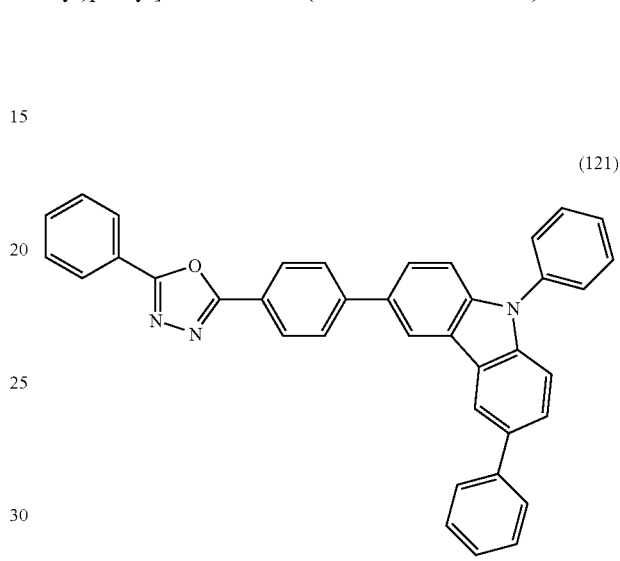

(121)

Into a 100 mL three-neck flask were put 1.0 g (2.8 mmol) of 2-iodophenyl-5-phenyl-1,3,4-oxadiazole (Compound a2), 1.0 g (2.8 mmol) of 6,9-diphenyl-9H-carbazol-3-boronic acid (Compound b2), and 0.060 g (0.20 mmol) of tri(o-tolyl)phosphine. Into the 100 mL three-neck flask were further added 15 mL of 1,2-dimethoxyethane (abbreviation: DME) and 5 mL of a 2M aqueous solution of potassium carbonate. Next, the obtained mixture was degassed under low pressure, the atmosphere in the 100 mL three-neck flask was substituted by nitrogen, 6.2 mg (0.028 mmol) of palladium(II) acetate was added into the mixture, and the mixture was stirred at 90° C. for 3 hours. After stirring, chloroform was added to the mixture, and a suspension was obtained. After this suspension was washed with saturated aqueous solution of sodium carbonate aqueous solution and brine in this order, magnesium sulfate was added to an organic layer to dry the organic layer. After drying, suction filtration was performed to remove magnesium sulfate in the organic layer, further suction filtration was performed through Celite (produced by Wako Pure Chemical Industries, Ltd., Catalog No. 531-16855), and a filtrate was obtained. A compound obtained by concentrating the filtrate was purified by silica gel column chromatography. The column chromatography was performed first using toluene as a developing solvent and then using a mixed solvent of toluene:ethyl acetate=4:1 as a developing solvent. The compound obtained by concentrating the obtained fractions was recrystallized with a mixed solvent of chloroform and methanol. As a result, 1.1 g of a powdery white solid was obtained in a yield of 73%. Synthesis Scheme (a-2) of this example is represented below.

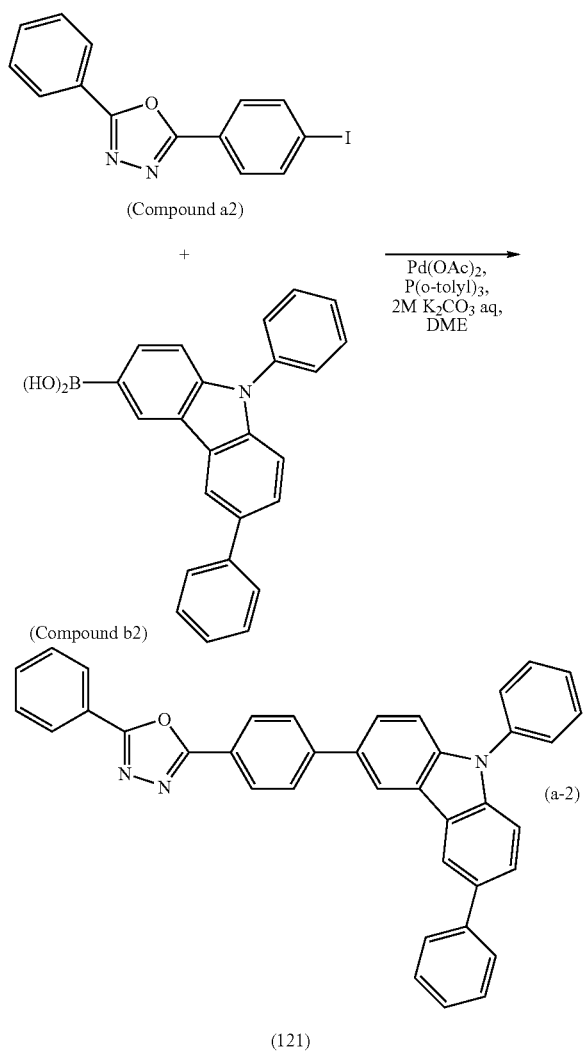

Sublimation purification of 1.1 g of the obtained solid was performed by a train sublimation method. The sublimation purification was conducted under a low pressure of 2.5 Pa, an argon flow rate of 5.0 mL/min, at 290° C. for 19 hours. The yield was 0.90 g (81%).

The compound obtained by the above method was measured by a nuclear magnetic resonance (NMR) method. The measurement data are as follows: $^1$H-NMR (CDCl$_3$, 300 MHz): δ=7.33-7.77 (m, 17H), 7.91 (d, J=8.8 Hz, 2H), 8.16-8.20 (m, 2H), 8.25 (d, J=8.8 Hz, 2H), 8.44 (sd, J=1.5 Hz, 1H), 8.48 (sd, J=1.5 Hz, 1H).

Figure 13A:
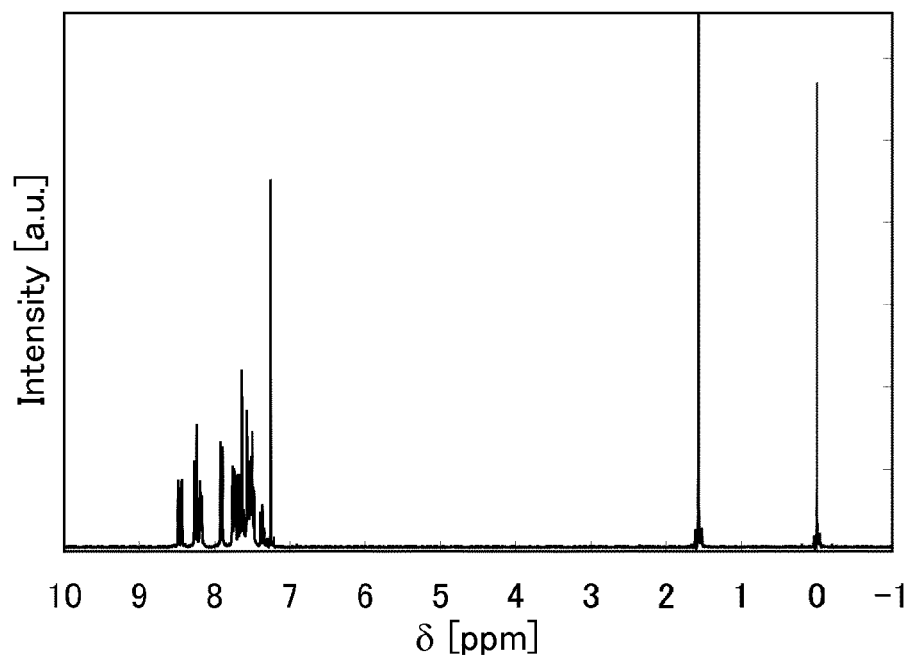
FIGS. 13A and 13B each show a $^1$H-NMR chart of PCO11II (abbreviation) represented by Structural Formula (121)
Figure 13B:
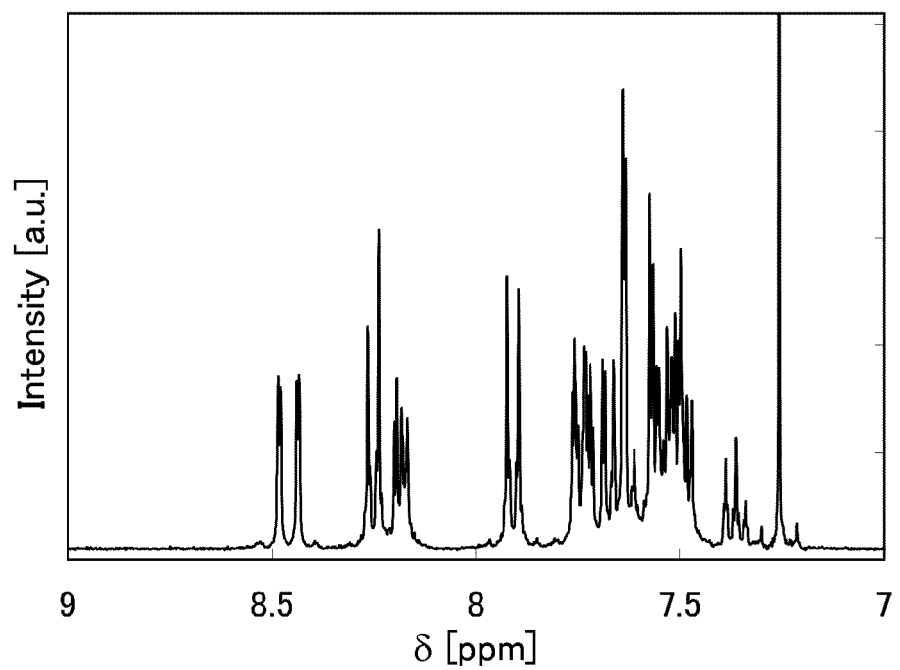

The $^1$H-NMR chart of the compound obtained by the above method is shown in FIGS. 13A and 13B. Note that FIG. 13B is a chart showing an enlarged view of the range of 7.0 ppm to 9.0 ppm in FIG. 13A. The measurement result indicates that 3,9-diphenyl-6-[4-(5-phenyl-1,3,4-oxadiazol-2-yl)phenyl]-9H-carbazole (abbreviation: PCO11II), which is the oxadiazole derivative represented by Structural Formula (121) above was obtained.

Figure 14A:
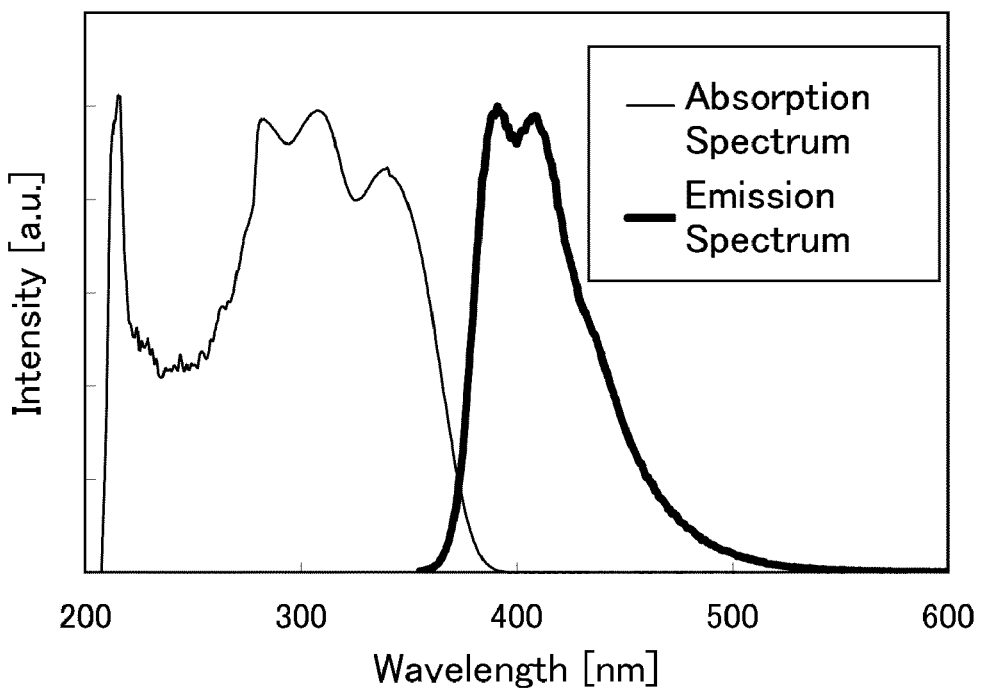
FIG. 14A shows an ultraviolet-visible absorption spectrum and an emission spectrum of a solution sample of PCO11II (abbreviation) represented by Structural Formula (121)
Figure 14B:
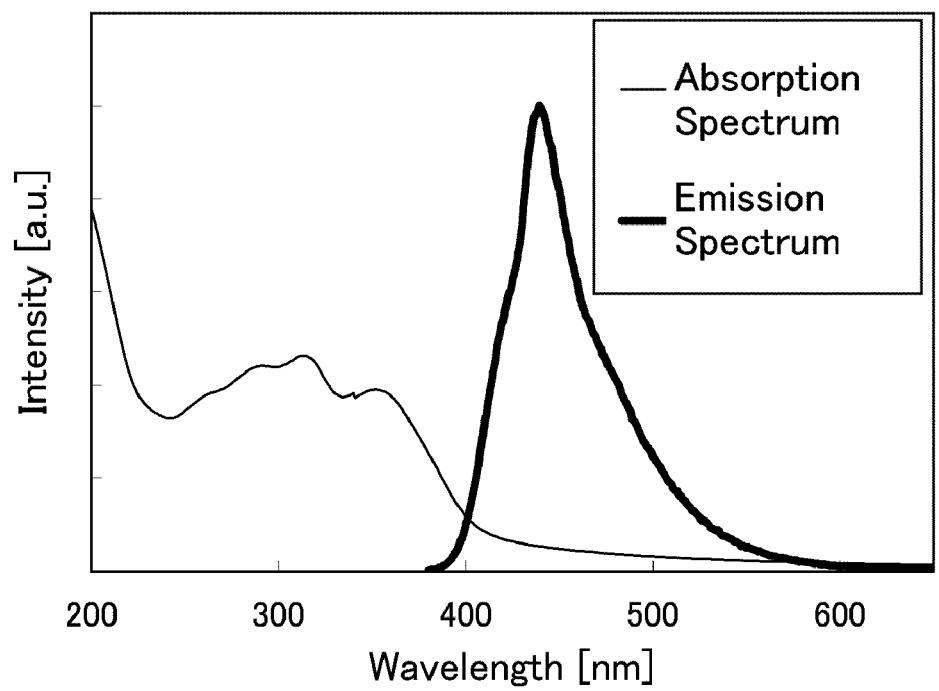
FIG. 14B shows an ultraviolet-visible absorption spectrum and an emission spectrum of a thin-film sample thereof.

FIGS. 14A and 14B show absorption spectra and emission spectra of PCO11II, which are measurement results using an ultraviolet-visible spectrophotometer. Note that the absorption spectra and the emission spectra of PCO11II were measured using a sample of a toluene solution of PCO11II in a quartz cell and a sample of a thin film of PCO11II which had been evaporated on a quartz substrate. Specifically, FIG. 14A shows spectra obtained using the solution sample, and FIG. 14B shows spectra obtained using the thin-film sample. In addition, for the purpose of evaluating only the absorption spectra from PCO11II, in the case of the solution sample, the absorption spectrum of FIG. 14A is obtained by subtracting the absorption spectra of quartz and toluene from the actually obtained absorption spectrum. As for the thin-film sample, the absorption spectrum of FIG. 14B is obtained by subtracting the absorption spectrum of quartz from the actually obtained absorption spectrum.

In FIGS. 14a and 14B, the horizontal axes indicate wavelength (nm) and the vertical axes indicate intensity (a given unit). In the case of the toluene solution sample, the absorption peak is observed at 336 nm, and the maximum emission wavelength is observed at 391 nm and 409 nm (excitation wavelength: 336 nm) (see FIG. 14A). In the case of the thin-film sample, the absorption peak is observed at 352 nm, and the maximum emission wavelength is observed at 440 nm (excitation wavelength: 352 nm) (see FIG. 14B).

A measurement result of the HOMO level and the LUMO level of the thin-film sample of PCO11II is shown. Specifically, first, the value of the ionization potential which had been measured with a photoelectron spectrometer (AC-2, produced by Riken Keiki Co., Ltd.) in air was converted into a negative value, and then the HOMO level was obtained. Next, the absorption edge was obtained from Tauc plot, with an assumption of direct transition, using data on the absorption spectrum in FIG. 14B, it was added as an optical energy gap to the value of the HOMO level, and then the LUMO level was obtained. As a result, the HOMO level of PCO11II was −5.61 eV, and the LUMO level thereof was −2.47 eV (the optical energy gap was 3.14 eV). PCO11II therefore was revealed to have a large energy gap.

Figure 15A:
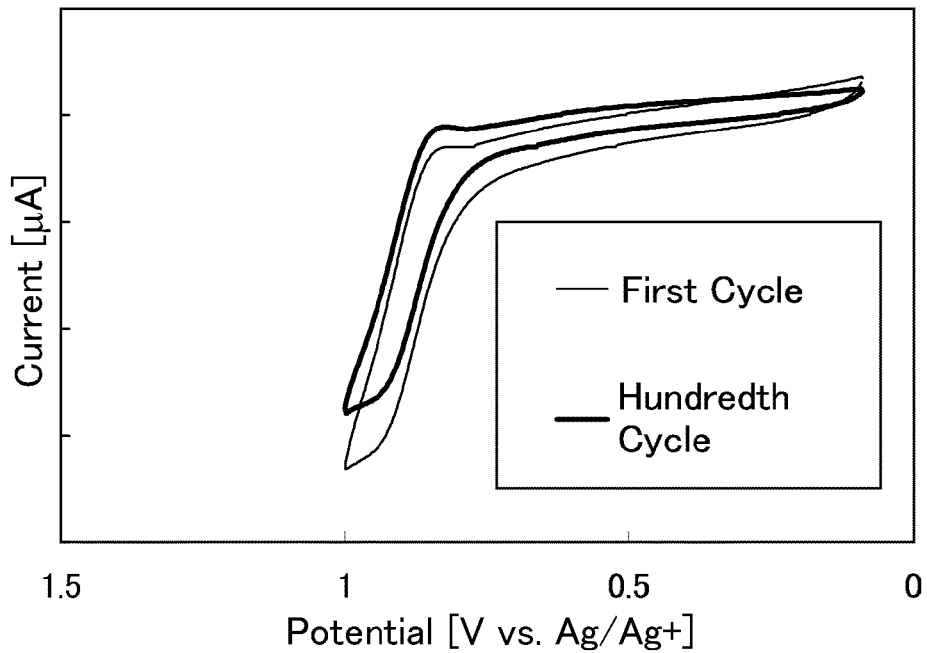
FIGS. 15A and 15B show oxidation characteristics and reduction characteristics, respectively, of PCO11II (abbreviation) represented by Structural Formula (121)
Figure 15B:
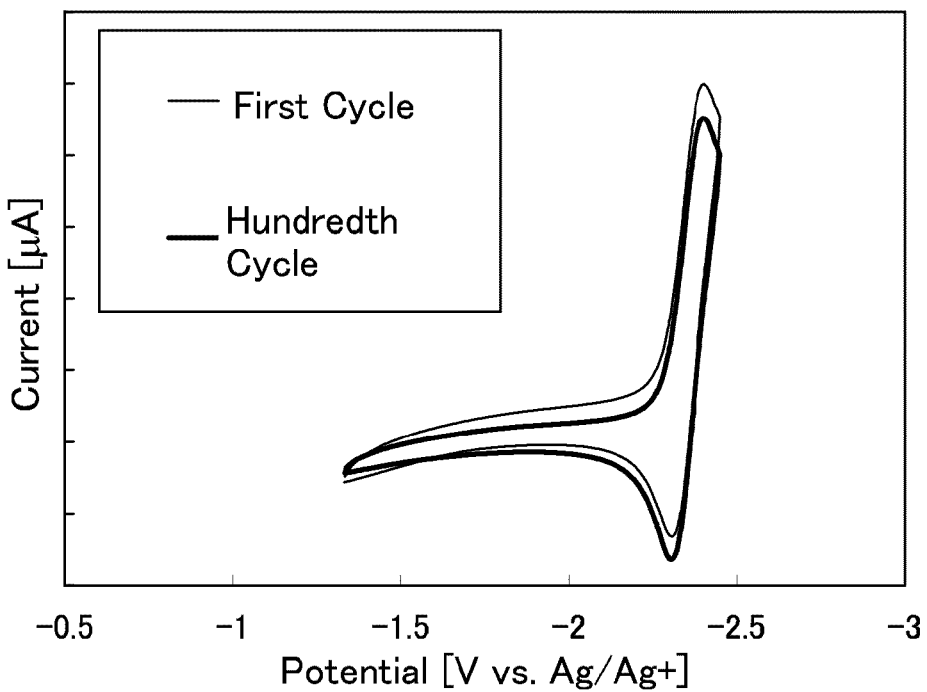

FIGS. 15A and 15B show measurement results of oxidation-reduction characteristics of PCO11II. Note that FIG. 15A shows oxidation characteristics, and FIG. 15B shows reduction characteristics. The oxidation-reduction reaction characteristics were measured by cyclic voltammetry (CV). Note that an electrochemical analyzer (ALS model 600A, produced by BAS Inc.) was used for the measurement.

For a solution used in the CV measurements, dehydrated dimethylformamide (DMF, produced by Sigma-Aldrich Inc., 99.8%, Catalog No. 22705-6) was used as a solvent. Tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, the concentration of PCO11II, which was to be measured, was adjusted to 1 mmol/L. In addition, a platinum electrode (PTE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE7 reference electrode for nonaqueous solvent, produced by BAS Inc.) was used as a reference electrode. Note that the measurements were conducted at room temperature.

The oxidation characteristics of PCO11II were examined as follows. A scan for changing the potential of the working electrode with respect to the reference electrode from 0.09 V to 1.00 V and then from 1.00 V to 0.09 V was set to one cycle, and the measurement was performed for 100 cycles. Note that the scanning speed of the CV measurement was set to be 0.1 V/s. In addition, FIG. 15A shows only the CV charts at the first cycle and the hundredth cycle.

The reduction characteristics of PCO11II were examined as follows. A scan for changing the potential of the working electrode with respect to the reference electrode from −1.33 V to −2.45 V and then from −2.45 V to −1.33 V was set to one cycle, and the measurement was performed for 100 cycles. Note that the scanning speed of the CV measurement was set to be 0.1 V/s. In addition, FIG. 15B shows only the CV charts at the first cycle and the hundredth cycle.

In each of FIGS. 15A and 15B, the horizontal axis shows potential (V) of the working electrode with respect to the reference electrode, while the vertical axis shows a value (μA) of current flowing between the working electrode and the auxiliary electrode. FIG. 15A reveals that PCO11II has a peak indicating oxidation at +0.89 V (vs. Ag/Ag+ electrode). In addition, FIG. 15B reveals that PCO11II has a peak indicating reduction at −2.36 V (vs. Ag/Ag+ electrode).

FIGS. 15A and 15B show no significant change in the position and intensity of the peaks in CV curves of the oxidation and reduction between the first cycle and the hundredth cycle, thereby indicating that PCO11II is stable to repetitive oxidation and reduction.

Figure 16A:
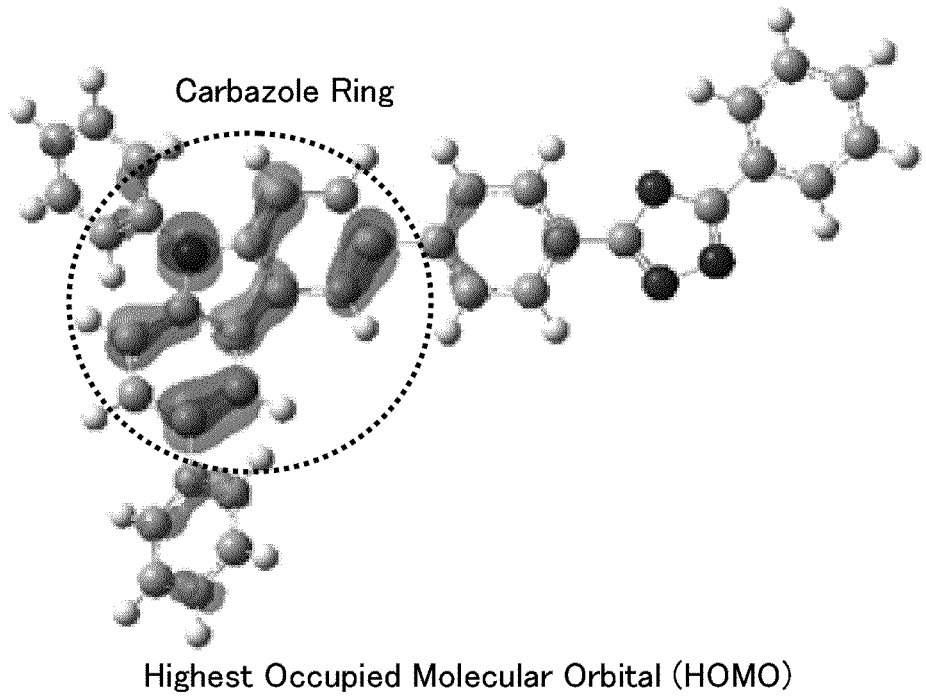
FIGS. 16A and 16B show a highest occupied molecular orbital (HOMO) and a lowest unoccupied molecular orbital (LUMO), respectively, of PCO11II (abbreviation) which are obtained by simulation.
Figure 16B:
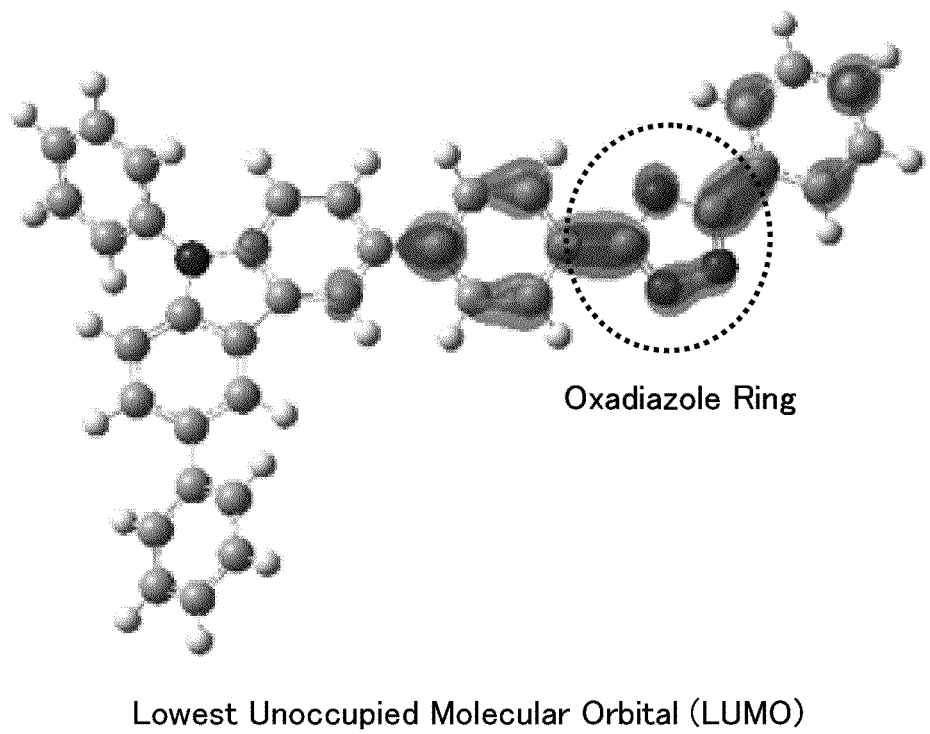

In addition, the optimal molecular structure of PCO11II in the ground state was obtained using the calculation similar to that in Example 1. FIGS. 16A and 16B show respectively the HOMO and the LUMO of PCO11II, which were found by the calculations.

FIGS. 16A and 16B reveal that the HOMO and the LUMO of PCO11II exist in a carbazole ring and an oxadiazole ring, respectively. In other words, the carbazole ring contributes to the hole-transport property of PCO11II while the oxadiazole ring contributes to the electron-transport property thereof. The carbazole ring is a unit exhibiting a high hole-transport property, and the oxadiazole ring is a unit exhibiting a high electron-transport property. From the above, it is found that PCO11II is bipolar.

Example 3

In this example, described are a method for manufacturing a light-emitting element including any of the oxadiazole derivatives described in Embodiment 1 as a host material and results of the element characteristics measurement. Specifically, Light-Emitting Element 1 formed using 9-phenyl-3-[4-(5-phenyl-1,3,4-oxadiazol-2-yl)phenyl]-9H-carbazole (abbreviation: PCO11), which is described in Example 1, and Light-Emitting Element 2 formed using 3,9-diphenyl-6-[4-(5-phenyl-1,3,4-oxadiazol-2-yl)phenyl]-9H-carbazole (abbreviation: PCO11II), which is described in Example 2, will be described.

Figure 17:
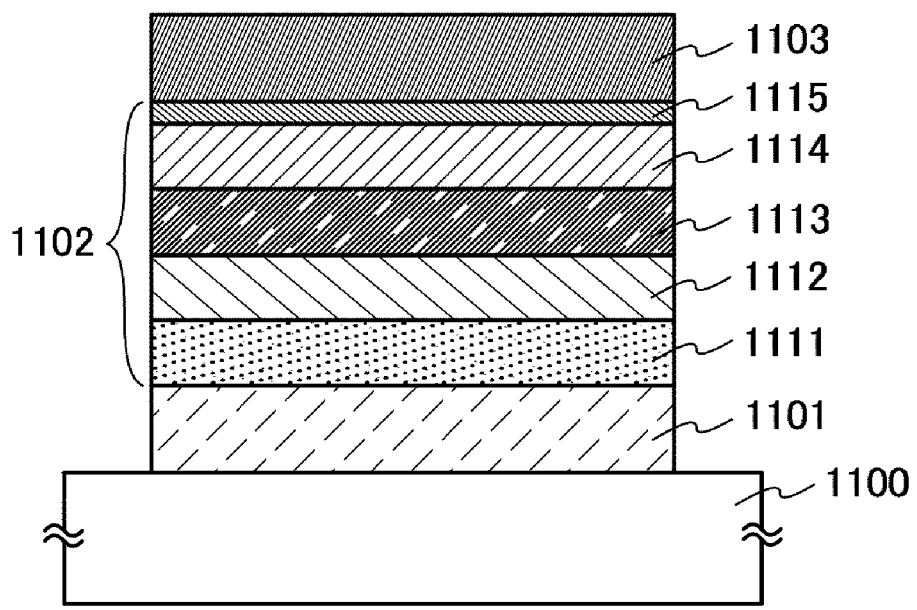
FIG. 17 illustrates a light-emitting element described in Example 3.

Note that each element structure of the light-emitting elements of this example is illustrated in FIG. 17, in which a light-emitting layer 1113 is formed using any of the oxadiazole derivatives described above. Structural formulas of organic compounds used in this example are shown below.

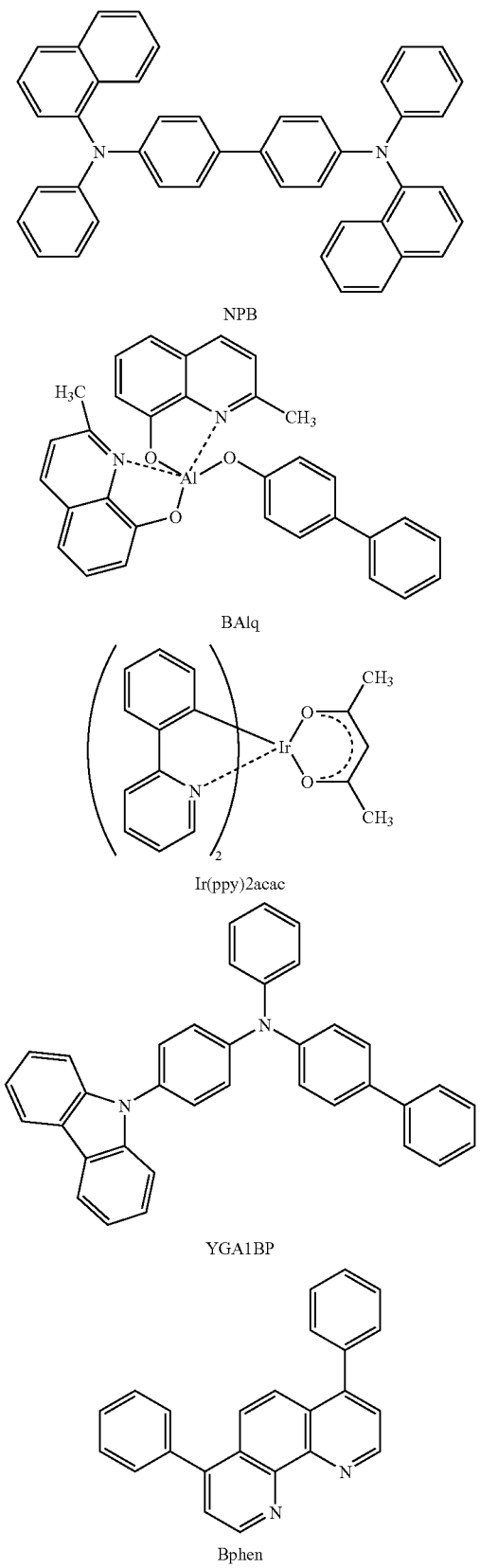

First, indium oxide-tin oxide containing silicon oxide was deposited on a substrate 1100 which was a glass substrate by a sputtering method to form a first electrode 1101. The thickness was 110 nm and the electrode area was 2 mm×2 mm.

Next, an EL layer 1102 in which a plurality of layers were stacked was formed over the first electrode 1101. In this example, the EL layer 1102 included a hole-injection layer 1111, a hole-transport layer 1112, a light-emitting layer 1113, an electron-transport layer 1114, and an electron-injection layer 1115, which were sequentially stacked.

The substrate 1100 provided with the first electrode 1101 was fixed on a substrate holder that was provided in a vacuum evaporation apparatus so that a surface provided with the first electrode 1101 faced downward. The pressure in the vacuum evaporation apparatus was reduced to approximately $10^{-4}$ Pa. Then, on the first electrode 1101, 4,4'-bis[N-(1-naphthyl)-N-phenylamino]biphenyl (abbreviation: NPB) and molybdenum(VI) oxide were co-evaporated to form the hole-injection layer 1111. The thickness of the hole-injection layer 1111 was 40 nm, and the evaporation rate was controlled so that the mass ratio of NPB to molybdenum(VI) oxide was 4:1 (=NPB: molybdenum oxide). Note that the co-evaporation method refers to an evaporation method in which evaporation is carried out from a plurality of evaporation sources at the same time in one treatment chamber.

Next, a 20-nm-thick film of a hole-transport material was formed on the hole-injection layer 1111 by an evaporation method with resistance heating to form the hole-transport layer 1112. Note that for the hole-transport layer 1112, 4-(9H-carbazol-9-yl)-4'-phenyltriphenylamine (abbreviation: YGAlBP) was used.

Next, the light-emitting layer 1113 was formed over the hole-transport layer 1112 by an evaporation method using resistance heating. As the light-emitting layer 1113 of Light-Emitting Element 1, PCO11 and bis(2-phenylpyridinato-N, $C^{2'}$)iridium(III) acetylacetonato (abbreviation: Ir(ppy)$_2$acac) were co-evaporated to form a 40-nm-thick film. Here, the evaporation rate was controlled so that the mass ratio of PCO11 to Ir(ppy)$_2$acac was 1:0.06 (=PCO11:Ir(ppy)$_2$acac). As the light-emitting layer 1113 of Light-Emitting Element 2, PCO11II and Ir(ppy)$_2$acac were co-evaporated to form a 40-nm-thick film. Here, the evaporation rate was controlled so that the mass ratio of PCO11II to Ir(ppy)$_2$acac was 1:0.06 (=PCO11II:Ir(ppy)$_2$acac).

Furthermore, on the light-emitting layer 1113, a 10-nm-thick film of bis(2-methyl-8-quinolinolato)(4-phenylphenolato)aluminum(III) (abbreviation: BAlq) and, thereon, a 20-nm-thick film of bathophenanthroline (abbreviation: BPhen) were formed by an evaporation method using resistance heating to form the electron-transport layer 1114.

Over the electron-transport layer 1114, the electron-injection layer 1115 was formed by depositing lithium fluoride (LiF) to a thickness of 1 nm.

Lastly, a 200-nm-thick film of aluminum was formed by an evaporation method using resistance heating to form the second electrode 1103. Light-Emitting Elements 1 and 2 were thus formed.

Thus obtained Light-Emitting Elements 1 and 2 were sealed in a glove box under a nitrogen atmosphere without being exposed to atmospheric air. Then, the operating characteristics of these light-emitting elements were measured. Note that the measurement was carried out at room temperature (in an atmosphere kept at 25° C.).

Figure 18:
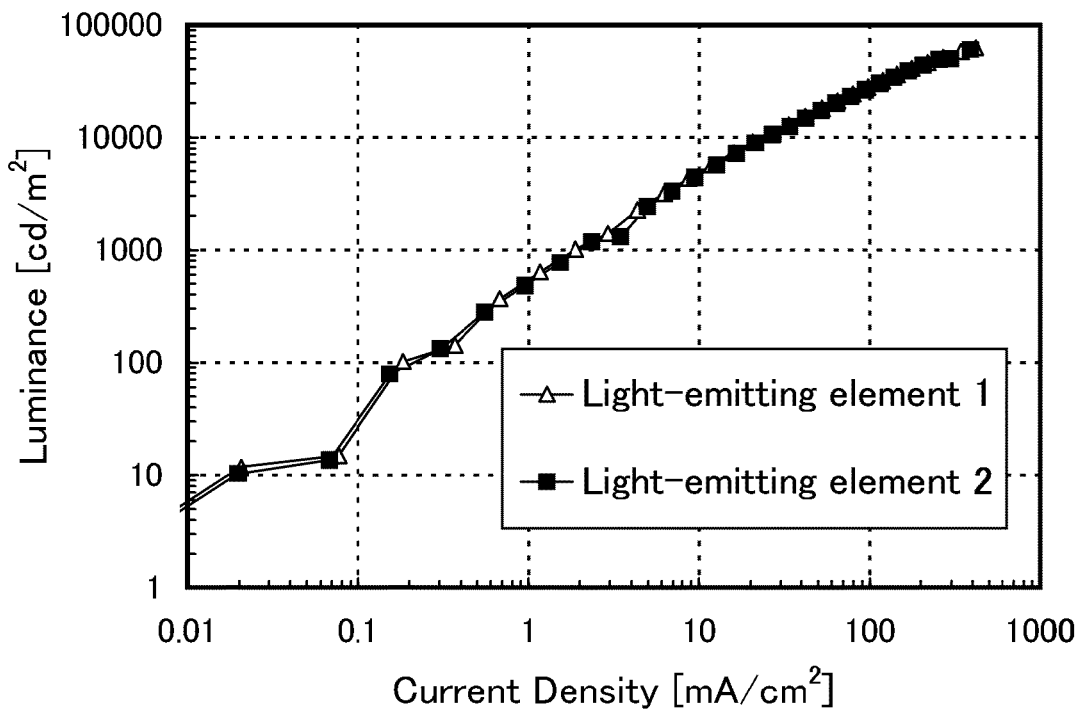
FIG. 18 shows current density-luminance characteristics of Light-Emitting Element 1 and Light-Emitting Element 2 described in Example 3.
Figure 19:
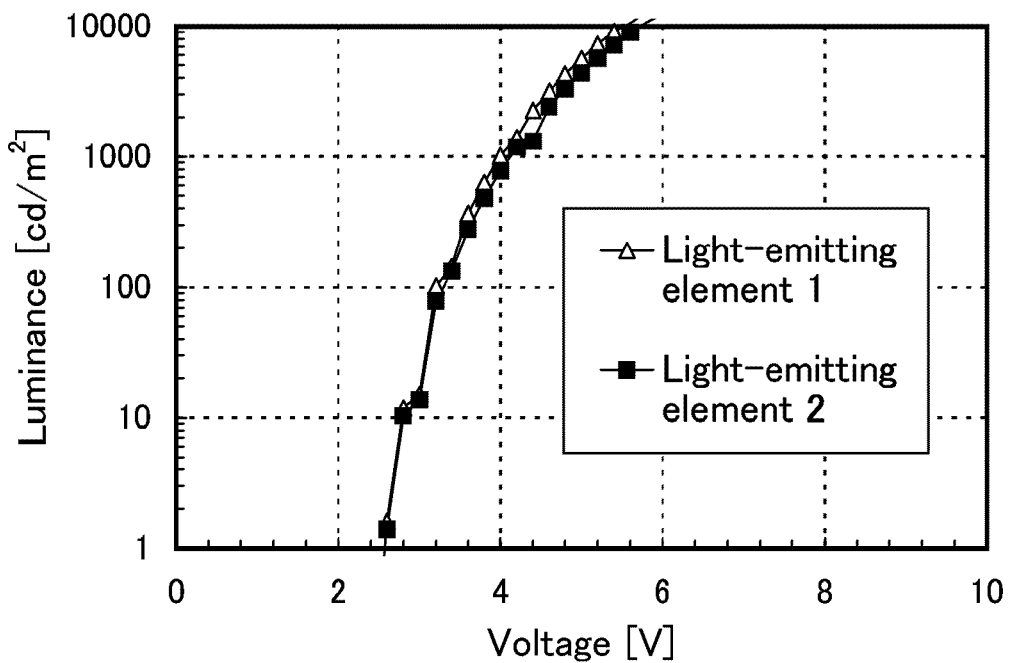
FIG. 19 shows voltage-luminance characteristics of Light-Emitting Element 1 and Light-Emitting Element 2 described in Example 3.
Figure 20:
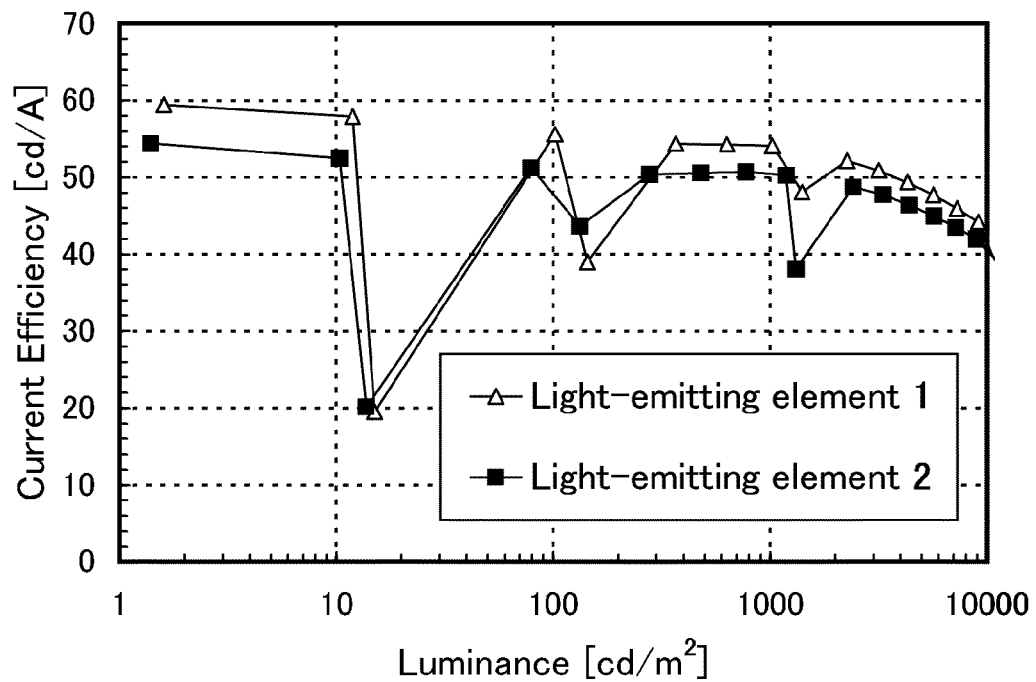
FIG. 20 shows luminance-current efficiency characteristics of Light-Emitting Element 1 and Light-Emitting Element 2 described in Example 3.

FIG. 18 shows current density-luminance characteristics of Light-Emitting Elements 1 and 2; FIG. 19 shows voltage-luminance characteristics thereof; and FIG. 20 shows luminance-current efficiency characteristics thereof. In FIG. 18, the vertical axis represents luminance (cd/m$^2$) and the horizontal axis represents current density (mA/cm$^2$). In FIG. 19, the vertical axis represents luminance (cd/m$^2$) and the horizontal axis represents voltage (V). In FIG. 20, the vertical axis represents current efficiency (cd/A) and the horizontal axis represents luminance (cd/m$^2$).

From FIG. 20, the maximum current efficiency of Light-Emitting Element 1 is 59 cd/A, and the maximum current efficiency of Light-Emitting Element 2 is 54 cd/A. This demonstrates that the light-emitting element including PCO11 or PCO11II has extremely high efficiency.

Figure 21:
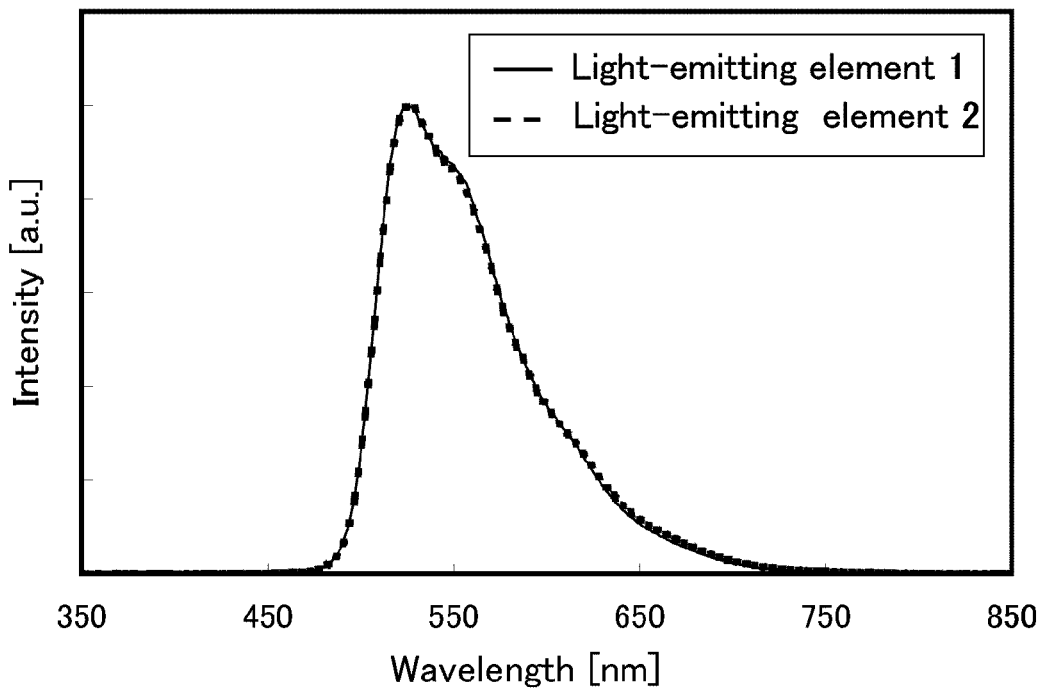
FIG. 21 shows emission spectra of Light-Emitting Element 1 and Light-Emitting Element 2 described in Example 3.

FIG. 21 shows emission spectra of Light-Emitting Element 1 and Light-Emitting Element 2. As shown in FIG. 21, in each case of Light-Emitting Elements 1 and 2, an emission wavelength provided by Ir(ppy)$_2$acac which was used as a guest material is observed, whereas an emission wavelength provided by PCO11 or PCO11II which was used as the host material is not observed. Thus, it is confirmed that PCO11 and PCO11II each serve as a bipolar host material of the light-emitting layer of the light-emitting element.

This application is based on Japanese Patent Application serial no. 2009-079914 filed with Japan Patent Office on Mar. 27, 2009, the entire contents of which are hereby incorporated by reference.

What is claimed is:

1. An oxadiazole derivative represented by Formula (G1),

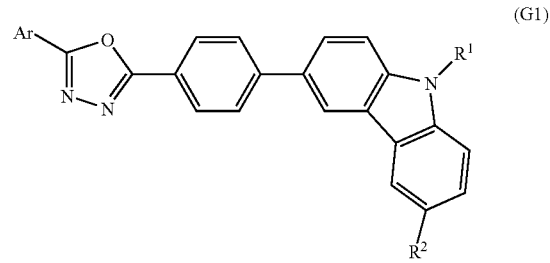

(G1)

wherein Ar represents a substituted or unsubstituted aryl group having 6 to 10 carbon atoms in a ring, wherein R$^1$ represents an alkyl group having 1 to 4 carbon atoms or a substituted or unsubstituted aryl group having 6 to 10 carbon atoms in a ring, and wherein R$^2$ represents hydrogen, an alkyl group having 1 to 4 carbon atoms, or a substituted or unsubstituted aryl group having 6 to 10 carbon atoms in a ring.

2. The oxadiazole derivative according to claim 1, wherein the oxadiazole derivative is represented by Formula (G2) below,

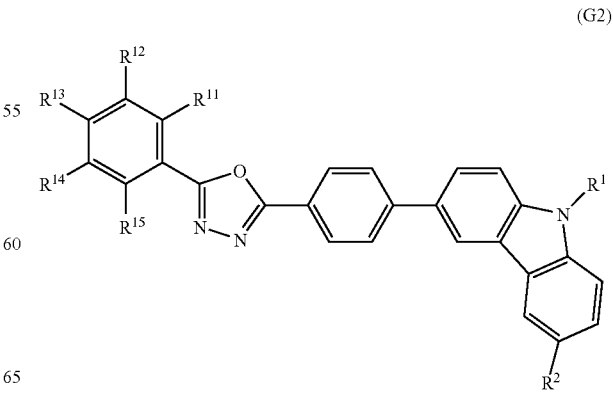

(G2)

wherein $R^{11}$ to $R^{15}$ each represent hydrogen, an alkyl group having 1 to 4 carbon atoms, or an aryl group having 6 to 10 carbon atoms in a ring.

3. The oxadiazole derivative according to claim 1, wherein the oxadiazole derivative is represented by Formula (G3) below,

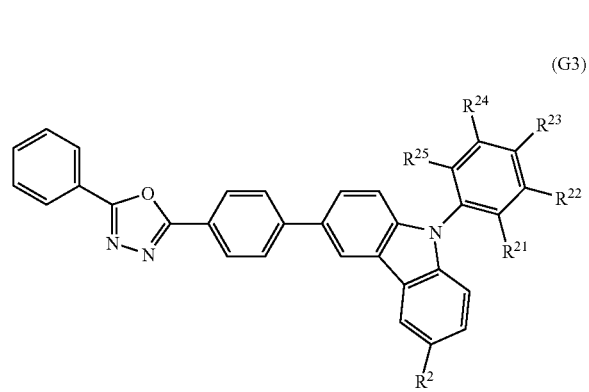

(G3)

wherein $R^{21}$ to $R^{25}$ each represent hydrogen, an alkyl group having 1 to 4 carbon atoms, or an aryl group having 6 to 10 carbon atoms in a ring.

4. The oxadiazole derivative according to claim 1, wherein the oxadiazole derivative is represented by Formula (G4) below,

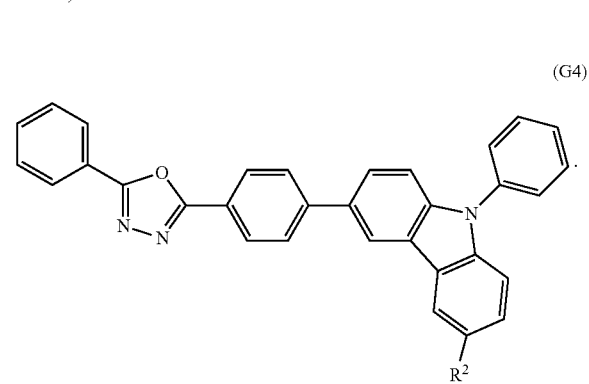

(G4)

5. A display device comprising a light-emitting element comprising an oxadiazole derivative represented by Formula (G1),

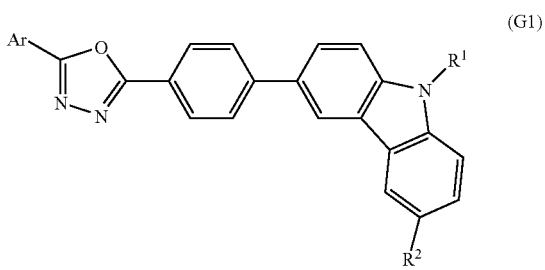

(G1)

wherein Ar represents a substituted or unsubstituted aryl group having 6 to 10 carbon atoms in a ring,
wherein $R^1$ represents an alkyl group having 1 to 4 carbon atoms or a substituted or unsubstituted aryl group having 6 to 10 carbon atoms in a ring, and
wherein $R^2$ represents hydrogen, an alkyl group having 1 to 4 carbon atoms, or a substituted or unsubstituted aryl group having 6 to 10 carbon atoms in a ring.

6. The display device according to claim 5, wherein the oxadiazole derivative is represented by Formula (G2),

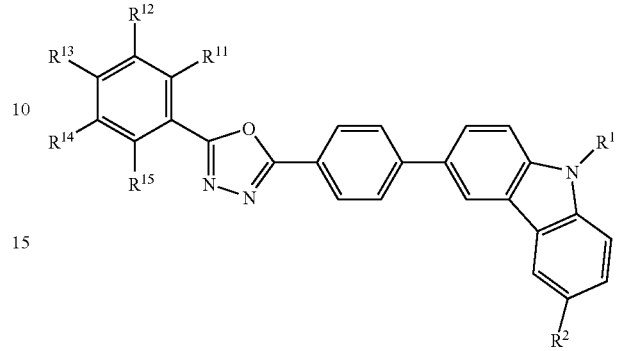

(G2)

wherein $R^{11}$ to $R^{15}$ each represent hydrogen, an alkyl group having 1 to 4 carbon atoms, or an aryl group having 6 to 10 carbon atoms in a ring.

7. The display device according to claim 5, wherein the oxadiazole derivative is represented by Formula (G3),

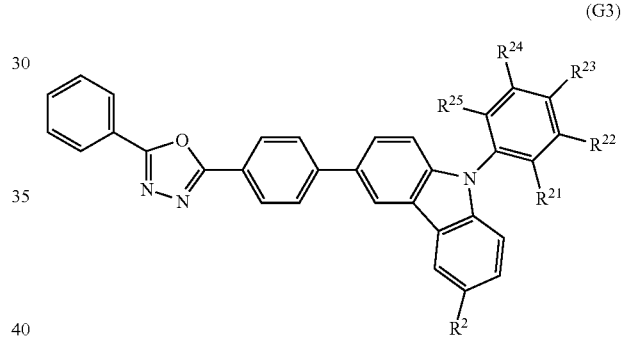

(G3)

wherein $R^{21}$ to $R^{25}$ each represent hydrogen, an alkyl group having 1 to 4 carbon atoms, or an aryl group having 6 to 10 carbon atoms in a ring.

8. The display device according to claim 5, wherein the oxadiazole derivative is represented by Formula (G4),

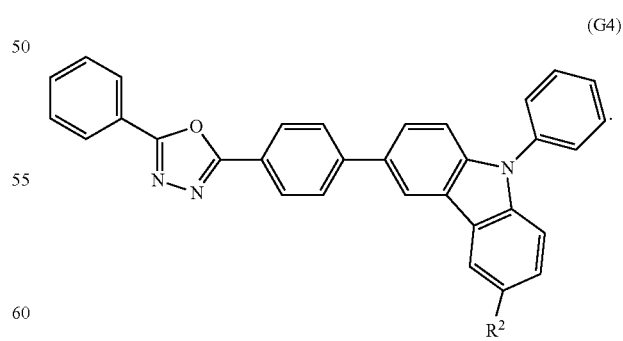

(G4)

9. The display device according to claim 5,
wherein the light-emitting element comprises a light-emitting layer, and
wherein the light-emitting layer comprises the oxadiazole derivative and a light-emitting substance.

10. The display device according to claim 9, wherein the light-emitting substance is a phosphorescent compound.

11. The display device according to claim 5, further comprising a controller for controlling light emission of the light-emitting element.

12. An electronic device comprising the display device according to claim 5 in a display portion.

13. A lighting device comprising a light-emitting element comprising an oxadiazole derivative represented by Formula (G1),

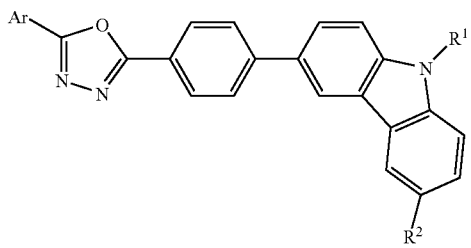

(G1)

wherein Ar represents a substituted or unsubstituted aryl group having 6 to 10 carbon atoms in a ring,
wherein $R^1$ represents an alkyl group having 1 to 4 carbon atoms or a substituted or unsubstituted aryl group having 6 to 10 carbon atoms in a ring, and
wherein $R^2$ represents hydrogen, an alkyl group having 1 to 4 carbon atoms, or a substituted or unsubstituted aryl group having 6 to 10 carbon atoms in a ring.

14. The lighting device according to claim 13, wherein the oxadiazole derivative is represented by Formula (G2),

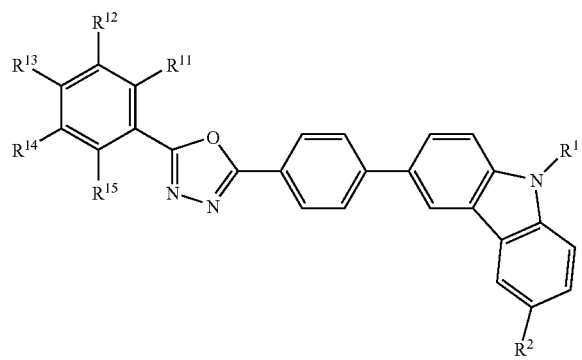

(G2)

wherein $R^{11}$ to $R^{15}$ each represent hydrogen, an alkyl group having 1 to 4 carbon atoms, or an aryl group having 6 to 10 carbon atoms in a ring.

15. The lighting device according to claim 13, wherein the oxadiazole derivative is represented by Formula (G3),

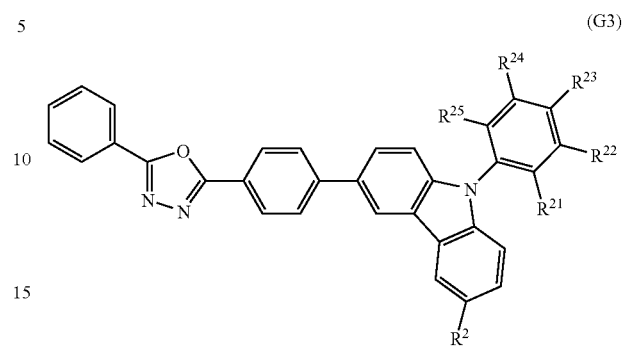

(G3)

wherein $R^{21}$ to $R^{25}$ each represent hydrogen, an alkyl group having 1 to 4 carbon atoms, or an aryl group having 6 to 10 carbon atoms in a ring.

16. The lighting device according to claim 13, wherein the oxadiazole derivative is represented by Formula (G4),

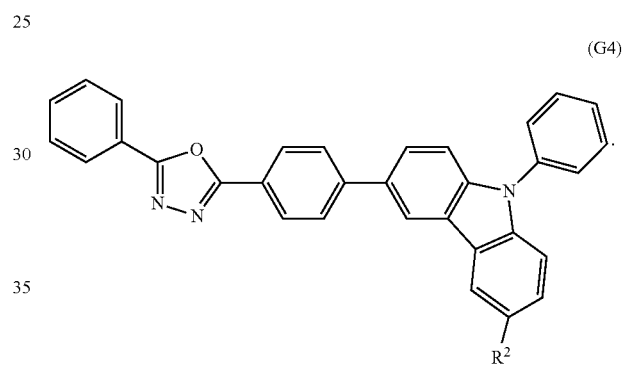

(G4)

17. The lighting device according to claim 13,
wherein the light-emitting element comprises a light-emitting layer, and
wherein the light-emitting layer comprises the oxadiazole derivative and a light-emitting substance.

18. The lighting device according to claim 17, wherein the light-emitting substance is a phosphorescent compound.

19. The lighting device according to claim 13, further comprising a controller for controlling light emission of the light-emitting element.

20. An electronic device comprising the lighting device according to claim 13 in an illuminating portion.

* * * * *